United States Patent
Betancourt

(10) Patent No.: US 12,343,322 B2
(45) Date of Patent: Jul. 1, 2025

(54) COMPOSITION AND METHOD FOR TREATING OR PROPHYLAXIS OF CORONAVIRUS AND CANCERS

(71) Applicant: BETAHEALTH LLC, Northbrook, IL (US)

(72) Inventor: Pablo Antonio Betancourt, Northbrook, IL (US)

(73) Assignee: BETAHEALTH LLC, Northbrook, IL (US)

( * ) Notice: Subject to any disclaimer, the term of this patent is extended or adjusted under 35 U.S.C. 154(b) by 418 days.

(21) Appl. No.: 17/412,523

(22) Filed: Aug. 26, 2021

(65) Prior Publication Data
US 2022/0062219 A1 Mar. 3, 2022

Related U.S. Application Data

(60) Provisional application No. 63/071,128, filed on Aug. 27, 2020, provisional application No. 63/104,621, filed on Oct. 23, 2020, provisional application No. 63/110,458, filed on Nov. 6, 2020, provisional application No. 63/110,485, filed on Nov. 6, 2020.

(51) Int. Cl.
| | |
|---|---|
| *A61K 38/06* | (2006.01) |
| *A61K 31/245* | (2006.01) |
| *A61K 38/46* | (2006.01) |
| *A61P 11/00* | (2006.01) |

(52) U.S. Cl.
CPC .......... *A61K 31/245* (2013.01); *A61K 38/063* (2013.01); *A61K 38/465* (2013.01); *A61P 11/00* (2018.01); *C12Y 301/21001* (2013.01)

(58) Field of Classification Search
CPC ... A61K 31/245; A61K 38/063; A61K 38/465
See application file for complete search history.

(56) References Cited

U.S. PATENT DOCUMENTS

| | | | |
|---|---|---|---|
| 6,172,053 B1 | 1/2001 | Fabunan | |
| 2006/0194221 A1* | 8/2006 | Skurkovich | C07K 16/249 435/6.16 |
| 2007/0128722 A1* | 6/2007 | Lin | C12N 5/0665 435/366 |
| 2015/0182667 A1* | 7/2015 | Guelcher | A61L 27/54 424/78.3 |
| 2019/0167680 A1 | 6/2019 | Sellar et al. | |
| 2020/0016231 A1* | 1/2020 | Kumar | A61K 38/063 |

FOREIGN PATENT DOCUMENTS

| | | |
|---|---|---|
| WO | 2015148768 A2 | 10/2015 |
| WO | WO-2020106709 A1 * | 5/2020 ............. A61K 38/00 |

OTHER PUBLICATIONS

Gilan et al. Extracellular DNA Plays an Important Structural Role in the Biofilm of the Plastic Degrading Actinomycete Rhodococcus Ruber; Advances in Microbiology, vol. 3, pp. 543-551/ (Year: 2013).*
Jones et al., "A Novel Endonuclease Inhibitor Exhibits Broad-Spectrum Anti-Influenza Virus Activity in Vitro", Antimicrobial Agents and Chemotherapy, vol. 60, No. 9, 2016, pp. 5504-5514.
Qiao et al., "Enhanced Binding of SARS-CoV-2 Spike Protein to Receptor by Distal Polybasic Cleavage Sites", ACS Nano, 2020, 8 pages.
Lee et al., "Long-acting nanoparticulate DNase-1 for effective suppresion of SARS-CoV-2-mediated neutrophil activities and cytokin storm", Biomaterials, vol. 267, 2021, pp. 1-10.
International Searching Authority Invitation to Pay Additional Fees for Application No. PCT/US21/47643 dated Nov. 9, 2021 (3 pages).
Papathanasiou et al., "Local Anesthetics and Covid19 Associated Acute Respiratory Distress Syndrome: A New Therapeutic Indication", Clinical Research: Open Access, 2020, vol. 6, No. 2, pp. 1-5.
Silvagno et al., "The Role of Glutathione in Protecting against the Severe Inflammatory Response Triggered by COVID-19", Antioxidants, 2020, vol. 9, No. 624, 16 pages.
Holliday, Study NCT04402970 Dornase ALfa for ARDS in Patients with SARS-CoV-2 (DORNASESARS2), 2020, <https://clinicaltrials.gov/ct2/show/NCT04402970>, 10 pages.
International Search Report and Written Opinion for Application No. PCT/US21/47643 dated Feb. 9, 2022 (21 pages).
Gentile et al., "Adipose Stem Cells (ACSs) and Stromal Vascular Fraction (SVF) as a Potential Therapy in Combating (COVID-19)-Disease", Aging and Disease, 2020, vol. 11, No. 3, pp. 465-469.
Ilinskaya et al., "Ribonucleases as Antiviral Agents", Molecular Biology, 2014, vol. 48, No. 5, pp. 615-623.
United States Patent Office Action for U.S. Appl. No. 18/306,483 dated Apr. 12, 2024 (1 page).
Horowitz et al. Efficacy of Glutathione Therapy in Relieving Dyspnea Associated With COVID-19 Pneumonia: A Report of 2 Cases; Respiratory Medicine Case Reports, vol. 30, pp. 1-7. (Year: 2020).
Earhart et al. Consideration of Dornase Alfa for the Treatment of Severe COVID-19 Acute Respiratory Distress Syndrome; New Microbe and New Infection, vol. 35, pp. 1-3. (Year: 2020).
European Patent Office Extended European Search Report for Application No. 21862692.7, dated Aug. 28, 2024 (9 pages).

(Continued)

*Primary Examiner* — Jeanette M Lieb
*Assistant Examiner* — Paul C Martin
(74) *Attorney, Agent, or Firm* — Michael Best & Friedrich LLP

(57) ABSTRACT

Described herein is a composition and methods for treating, reducing the symptoms of, or prophylaxis of viral infections, and particularly SARS-COV-2. The composition enhances delivery of oxygen to the tissues. Also described herein is a composition and methods for treating cancers, particularly, adenocarcinomas, infiltrating ductal adenocarcinoma, metastatic ductal adenocarcinoma, and neuroendocrine tumors. The composition inhibits the growth of tumor cells and promotes cytoreduction of tumors.

18 Claims, 3 Drawing Sheets

Specification includes a Sequence Listing.

(56) References Cited

OTHER PUBLICATIONS

Hawes, M. C. et al. "Extracellular DNA: a bridge to cancer." Cancer research 75.20 (2015): 4260-4264.
Traverso, N., et al. "Role of glutathione in cancer progression and chemoresistance." Oxidative medicine and cellular longevity Jan. 2013 (2013): 972913.
Villar-Garea, A., et al. "Procaine is a DNA-demethylating agent with growth-inhibitory effects in human cancer cells." Cancer research 63.16 (2003): 4984-4989.

* cited by examiner

```
                        SEQUENCE LISTING

<160> NUMBER OF SEQ ID NOS: 5

<210> SEQ ID NO 1
<211> LENGTH: 282
<212> TYPE: PRT
<213> ORGANISM: Homo sapiens

<400> SEQUENCE: 1

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270
```

```
Asp His Tyr Pro Val Glu Val Met Leu Lys
            275                 280

<210> SEQ ID NO 2
<211> LENGTH: 260
<212> TYPE: PRT
<213> ORGANISM: Artificial Sequence
<220> FEATURE:
<223> OTHER INFORMATION: Recombinant Human DNase 1

<400> SEQUENCE: 2

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 3
<211> LENGTH: 282
<212> TYPE: PRT
<213> ORGANISM: Bos taurus

<400> SEQUENCE: 3

Met Arg Gly Thr Arg Leu Met Gly Leu Leu Leu Ala Leu Ala Gly Leu
1               5                   10                  15

Leu Gln Leu Gly Leu Ser Leu Lys Ile Ala Ala Phe Asn Ile Arg Thr
            20                  25                  30
```

-continued

Phe Gly Glu Thr Lys Met Ser Asn Ala Thr Leu Ala Ser Tyr Ile Val
            35                  40                  45

Arg Ile Val Arg Arg Tyr Asp Ile Val Leu Ile Gln Glu Val Arg Asp
 50                  55                  60

Ser His Leu Val Ala Val Gly Lys Leu Leu Asp Tyr Leu Asn Gln Asp
 65                  70                  75                  80

Asp Pro Asn Thr Tyr His Tyr Val Val Ser Glu Pro Leu Gly Arg Asn
                 85                  90                  95

Ser Tyr Lys Glu Arg Tyr Leu Phe Leu Phe Arg Pro Asn Lys Val Ser
            100                 105                 110

Val Leu Asp Thr Tyr Gln Tyr Asp Asp Gly Cys Glu Ser Cys Gly Asn
            115                 120                 125

Asp Ser Phe Ser Arg Glu Pro Ala Val Val Lys Phe Ser Ser His Ser
130                 135                 140

Thr Lys Val Lys Glu Phe Ala Ile Val Ala Leu His Ser Ala Pro Ser
145                 150                 155                 160

Asp Ala Val Ala Glu Ile Asn Ser Leu Tyr Asp Val Tyr Leu Asp Val
                165                 170                 175

Gln Gln Lys Trp His Leu Asn Asp Val Met Leu Met Gly Asp Phe Asn
            180                 185                 190

Ala Asp Cys Ser Tyr Val Thr Ser Ser Gln Trp Ser Ser Ile Arg Leu
            195                 200                 205

Arg Thr Ser Ser Thr Phe Gln Trp Leu Ile Pro Asp Ser Ala Asp Thr
            210                 215                 220

Thr Ala Thr Ser Thr Asn Cys Ala Tyr Asp Arg Ile Val Val Ala Gly
225                 230                 235                 240

Ser Leu Leu Gln Ser Ser Val Val Pro Gly Ser Ala Ala Pro Phe Asp
                245                 250                 255

Phe Gln Ala Ala Tyr Gly Leu Ser Asn Glu Met Ala Leu Ala Ile Ser
            260                 265                 270

Asp His Tyr Pro Val Glu Val Thr Leu Thr
            275                 280

<210> SEQ ID NO 4
<211> LENGTH: 156
<212> TYPE: PRT
<213> ORGANISM: Homo sapiens
<220> FEATURE:
<221> NAME/KEY: PROPEP
<222> LOCATION: (1)..(156)
<220> FEATURE:
<221> NAME/KEY: MISC_FEATURE
<222> LOCATION: (1)..(28)
<223> OTHER INFORMATION: Precursor; residues 1-28 removed in active form
<220> FEATURE:
<221> NAME/KEY: MISC_FEATURE
<222> LOCATION: (29)..(156)
<223> OTHER INFORMATION: Active RNase A

<400> SEQUENCE: 4

Met Ala Leu Glu Lys Ser Leu Val Arg Leu Leu Leu Leu Val Leu Ile
 1               5                  10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
            35                  40                  45

Ser Ser Ser Thr Tyr Cys Asn Gln Met Met Arg Arg Arg Asn Met Thr
 50                  55                  60

```
Gln Gly Arg Cys Lys Pro Val Asn Thr Phe Val His Glu Pro Leu Val
 65                  70                  75                  80

Asp Val Gln Asn Val Cys Phe Gln Glu Lys Val Thr Cys Lys Asn Gly
                 85                  90                  95

Gln Gly Asn Cys Tyr Lys Ser Asn Ser Ser Met His Ile Thr Asp Cys
                100                 105                 110

Arg Leu Thr Asn Gly Ser Arg Tyr Pro Asn Cys Ala Tyr Arg Thr Ser
            115                 120                 125

Pro Lys Glu Arg His Ile Ile Val Ala Cys Glu Gly Ser Pro Tyr Val
        130                 135                 140

Pro Val His Phe Asp Ala Ser Val Glu Asp Ser Thr
145                 150                 155

<210> SEQ ID NO 5
<211> LENGTH: 150
<212> TYPE: PRT
<213> ORGANISM: Bos taurus
<220> FEATURE:
<221> NAME/KEY: PROPEP
<222> LOCATION: (1)..(150)
<220> FEATURE:
<221> NAME/KEY: PROPEP
<222> LOCATION: (1)..(26)
<223> OTHER INFORMATION: Precursor; residues 1-26 removed in active form
<220> FEATURE:
<221> NAME/KEY: PROPEP
<222> LOCATION: (27)..(150)
<223> OTHER INFORMATION: Active RNase A

<400> SEQUENCE: 5

Met Ala Leu Lys Ser Leu Val Leu Leu Ser Leu Leu Val Leu Val Leu
  1               5                  10                  15

Leu Leu Val Arg Val Gln Pro Ser Leu Gly Lys Glu Thr Ala Ala Ala
             20                  25                  30

Lys Phe Glu Arg Gln His Met Asp Ser Ser Thr Ser Ala Ala Ser Ser
             35                  40                  45

Ser Asn Tyr Cys Asn Gln Met Met Lys Ser Arg Asn Leu Thr Lys Asp
         50                  55                  60

Arg Cys Lys Pro Val Asn Thr Phe Val His Glu Ser Leu Ala Asp Val
 65                  70                  75                  80

Gln Ala Val Cys Ser Gln Lys Asn Val Ala Cys Lys Asn Gly Gln Thr
                 85                  90                  95

Asn Cys Tyr Gln Ser Tyr Ser Thr Met Ser Ile Thr Asp Cys Arg Glu
                100                 105                 110

Thr Gly Ser Ser Lys Tyr Pro Asn Cys Ala Tyr Lys Thr Thr Gln Ala
            115                 120                 125

Asn Lys His Ile Ile Val Ala Cys Glu Gly Asn Pro Tyr Val Pro Val
        130                 135                 140

His Phe Asp Ala Ser Val
145                 150
```

COMPOSITION AND METHOD FOR TREATING OR PROPHYLAXIS OF CORONAVIRUS AND CANCERS

CROSS-REFERENCE TO RELATED APPLICATIONS

This application claims priority to U.S. Provisional Patent Application Nos. 63/071,128, filed on Aug. 27, 2020; 63/104,621, filed on Oct. 23, 2020; and 63/110,458 and 63/110,485, both filed on Nov. 6, 2020, each of which is incorporated by reference herein in its entirety.

REFERENCE TO SEQUENCE LISTING

This application is filed with a Computer Readable Form of a Sequence Listing in accordance with 37 C.F.R. § 1.821 (c). The text file submitted by EFS, "216882-9001-US05_sequence_listing_24 Aug. 2021_ST25.txt," was created on Aug. 24, 2021, contains 5 sequences, has a file size of 10.6 Kbytes, and is hereby incorporated by reference in its entirety.

TECHNICAL FIELD

Described herein is a composition and methods for treating, reducing the symptoms of, or prophylaxis of viral infections, and particularly SARS-COV-2. The composition enhances delivery of oxygen to the tissues. Also described herein is a composition and methods for treating cancers, particularly, adenocarcinomas, infiltrating ductal adenocarcinoma, metastatic ductal adenocarcinoma, and neuroendocrine tumors. The composition inhibits the growth of tumor cells and promotes cytoreduction of tumors.

BACKGROUND

Coronaviruses (CoVs), are enveloped positive-sense RNA viruses, which are surrounded by crown-shaped, club-like spikes projecting from the outer surface. Coronavirus spikes contain glycoproteins that are embedded over the viral envelope. The spike proteins bind to specific cellular angiotensin-converting enzyme 2 (ACE2) receptors; the binding initiates structural changes to spike protein that prompts penetration of cell membranes, which results in the release of the viral nucleocapsid into the cell. These spike proteins determine host trophism. Coronaviruses have a large RNA genome, ranging in size from 26 to 32 kilobases and capable replication in distinct ways. Like other RNA viruses, coronaviruses undergo replication of the genome and transcription of mRNAs upon infection. Coronavirus infection in a subject can result in significant and long-term damage of the lungs, leading to possibly severe respiratory issues.

The world-wide 2020 coronavirus (COVID-19) outbreak is caused by the SARS-COV-2 virus. The virus enters host cells by an interaction between the viral spike protein receptor binding domain and the host cell angiotensin-converting enzyme 2 (ACE2) receptor.

Pharmaceutical compositions are needed that can disrupt the interaction between the SARS-COV-2 virus and host cell and that, in turn, can be used to treat or prevent coronavirus infections.

Adenocarcinoma is a cancer that forms in mucus-secreting glands throughout the body. The disease may develop in many different tissues, but it is most prevalent in the following tissues: lung, prostate, cervix, breast, pancreas, esophagus, stomach, colon, rectum, among other tissues. Invasive ductal carcinoma is the most common form of breast cancer. Adenocarcinomas are typically treated by surgical removal, radiation therapy, chemotherapy, or a combination of these approaches.

Pharmaceutical compositions are needed that can inhibit the growth of adenocarcinomas and non-endocrine tumors and that promote cytoreduction of the tumors.

SUMMARY

One embodiment described herein is a pharmaceutical composition comprising: procaine or a pharmaceutically acceptable salt thereof; a tri- or tetra-peptide comprising one or more glutamate residues or a pharmaceutically acceptable salt thereof; DNase 1 or a pharmaceutically acceptable salt thereof. In one embodiment the composition further comprises RNase A, or a pharmaceutically acceptable salt thereof. In another embodiment the composition further comprises one or more pharmaceutically acceptable excipients. In another embodiment the composition comprises: about 5-15% by mass procaine or a pharmaceutically acceptable salt thereof; about 85-95% by mass of a tri- or tetra-peptide comprising one or more glutamate residues or a pharmaceutically acceptable salt thereof; about 0.01-0.1% by mass DNase 1 or a pharmaceutically acceptable salt thereof. In another embodiment the composition further comprises about 0.1-1.0% by mass RNase A, or a pharmaceutically acceptable salt thereof. In another embodiment the composition comprises: about 8-10% by mass procaine or a pharmaceutically acceptable salt thereof; about 88-92% by mass of a tri- or tetra-peptide comprising one or more glutamate residues or a pharmaceutically acceptable salt thereof; and about 0.02-0.08% by mass DNase 1 or a pharmaceutically acceptable salt thereof. In another embodiment the composition further comprises about 0.2-0.8% by mass RNase A, or a pharmaceutically acceptable salt thereof. In another embodiment the composition comprises: about 9% by mass procaine or a pharmaceutically acceptable salt thereof; about 90% by mass of a tri- or tetra-peptide comprising one or more glutamate residues or a pharmaceutically acceptable salt thereof; and about 0.05% by mass DNase 1 or a pharmaceutically acceptable salt thereof. In another embodiment the composition further comprises about 0.5% by mass RNase A or a pharmaceutically acceptable salt thereof. In another embodiment the composition comprises about 0.1-0.3 mg/ml procaine; about 1-3 mg/ml of a tri- or tetra-peptide comprising one or more glutamate residues; and about 0.0008-0.0012 mg/ml DNase 1. In another embodiment the composition further comprises and about 0.008-0.012 mg/mL RNase A. In another embodiment the composition comprises about 0.2 mg/ml procaine; about 2 mg/ml of a tri- or tetra-peptide comprising one or more glutamate residues; and about 0.001 mg/mL DNase 1. In another embodiment the composition further comprises and about 0.01 mg/ml by mass RNase A. In another embodiment the tri- or tetra-peptide comprising one or more glutamate residues comprises glutathione, E-E-X, X-E-E, E-X-E, E-E-X-X, E-E-X-E, E-X-E-E, E-X-X-E, X-E-E-E, or X-X-E-E, wherein E is a glutamate residue and X is any amino acid, and preferably an aliphatic amino acid. In another embodiment the tri- or tetra-peptide comprising one or more glutamate residues comprises glutathione (γE-C-G). In another embodiment the composition comprises: 9.0% by mass procaine; 90.4% by mass glutathione; and 0.05% by mass DNase 1. In another embodiment the composition further comprises 0.54% by mass RNase A. In another embodiment the composition comprises: 0.17 mg/ml procaine (0.71 mM); 1.7 mg/mL glutathione (5.4 mM); 0.001 mg/mL (0.3 µM) DNase 1. In another embodiment the composition further comprises 0.01 mg/ml (0.07 µM) RNase A. In another embodiment the composition is a liquid suitable for injection or inhalation. In another embodiment the composition further comprises or is co-administered with one or more stem cells. In another embodiment the stem cell is an embryonic stem cell, perinatal stem cell, adult stem cell, induced pluripotent stem cell, tissue-specific stem cell, mesenchymal stem cell, hematopoietic stem cell, mesenchymal stem cell, neural stem cell, or epithelial stem cell. In another embodiment the stem cell is a mesenchymal stem cell. In another embodiment the stem cell is a subject-derived stem cell.

Another embodiment described herein is a method or means for treating, reducing the symptoms of, or prophylaxis of a viral infection, the method comprising administering a therapeutically effective amount of a composition described herein to a subject in need thereof.

In another embodiment the viral infection is a coronavirus or a respiratory virus. In another embodiment the viral infection is SARS-COV-2. In another embodiment 1000 IU (10 mL) per day of the composition are administered to the subject in need thereof as a treatment. In another embodiment 100 IU (1 mL) per day of the composition are administered to the subject in need thereof as a prophylactic. In another embodiment the therapeutically effective amount of the composition is administered daily for 1 to 60 days. In another embodiment the therapeutically effective amount of the composition is administered by injection, infusion, or inhalation. In another embodiment the therapeutically effective amount of the composition is administered as a dosage regimen comprising one dose per day (QD), two doses per day (BID), three doses per day (TID), or four doses per day (QID) to achieve a total daily dosage.

Another embodiment described herein is the use of a composition described herein as a medicament for treating, reducing the symptoms of, or prophylaxis of a viral infection.

Another embodiment described herein is a method for increasing the $SpO_2$ of a subject suffering from a respiratory virus infection, the method comprising administering a therapeutically effective dose of a composition comprising procaine or a pharmaceutically acceptable salt thereof; glutathione a pharmaceutically acceptable salt thereof; and DNase 1 or a pharmaceutically acceptable salt thereof.

Another embodiment described herein is a method for manufacturing a pharmaceutical composition, the method comprising: combining procaine, a tri- or tetra-peptide comprising one or more glutamate residues, DNase 1; and filing the pharmaceutical composition into a receptacle for storage or administration.

Another embodiment described herein is a pharmaceutical composition produced by the method the described herein.

Another embodiment described herein is a method for treating adenocarcinoma or prophylaxis of recurrence thereof, the method comprising administering a therapeutically effective amount of a composition described herein to a subject in need thereof. In another embodiment the adenocarcinoma is infiltrating ductal adenocarcinoma, metastatic ductal adenocarcinoma, or neuroendocrine tumors. In another embodiment the adenocarcinoma is infiltrating ductal adenocarcinoma. In another embodiment a dose of 1000 IU (10 mL) per day of the composition is administered to the subject in need thereof as a treatment. In another embodiment the treatment is administered daily for 1 to 180 days. In another embodiment the treatment is administered by administering a portion of the dose intravenously and a portion of the dose is injected directly into an adenocarcinoma tumor. In another embodiment 70% of the dose is administered intravenously and 30% of the dose is injected directly into the adenocarcinoma tumor. In another embodiment the treatment is administered until a size of the adenocarcinoma tumor is reduced. In another embodiment the treatment is combined with a chemotherapeutic agent, radiation, or a combination thereof. In another embodiment the adenocarcinoma tumor is surgically removed following a reduction of size. In another embodiment a dose of 1000 IU (10 mL) per day or per week of the composition is administered to the subject in need thereof as a prophylactic. In another embodiment the dose is administered daily for 30 days to 180 days. In another embodiment the dose is administered weekly for 1 week to 52 weeks. In another embodiment the dose is administered monthly for 1 month to 48 months.

Another embodiment described herein is the use of a composition described herein as a medicament for treating adenocarcinoma or prophylaxis of recurrence thereof.

Another embodiment described herein is a method for inhibiting growth or causing cytoreduction of an adenocarcinoma, the method comprising contacting an adenocarcinoma with a composition described herein.

BRIEF DESCRIPTION OF THE DRAWINGS

FIG. 2A shows an image of the subject's lungs before treatment with TRESCELIUM™. The circled area indicates damage to the left lung associated with COVID-19 pneumonia. Comorbidities of the subject included obesity, diabetes, hypertension, and several allergies. FIG. 2B shows an image of the same lung 10 days after the subject was administered one dose of TRESCELIUM™. The circled area indicates the improved area of the left lung. Oxygen concentration at the time of TRESCELIUM™ treatment was 88%.

FIG. 3A shows an image of the subject's lungs before treatment with TRESCELIUM™. The circled area indicates damage to the left lung associated with COVID-19 pneumonia. Comorbidities of the subject included obesity, diabetes, and hypertension. FIG. 3B shows an image of the same lung eight days after the subject was administered one dose of TRESCELIUM™. The circled area indicates the improved area of the left lung. Oxygen saturation at the time of TRESCELIUM™ treatment was 90%.

DETAILED DESCRIPTION

Figure 1:
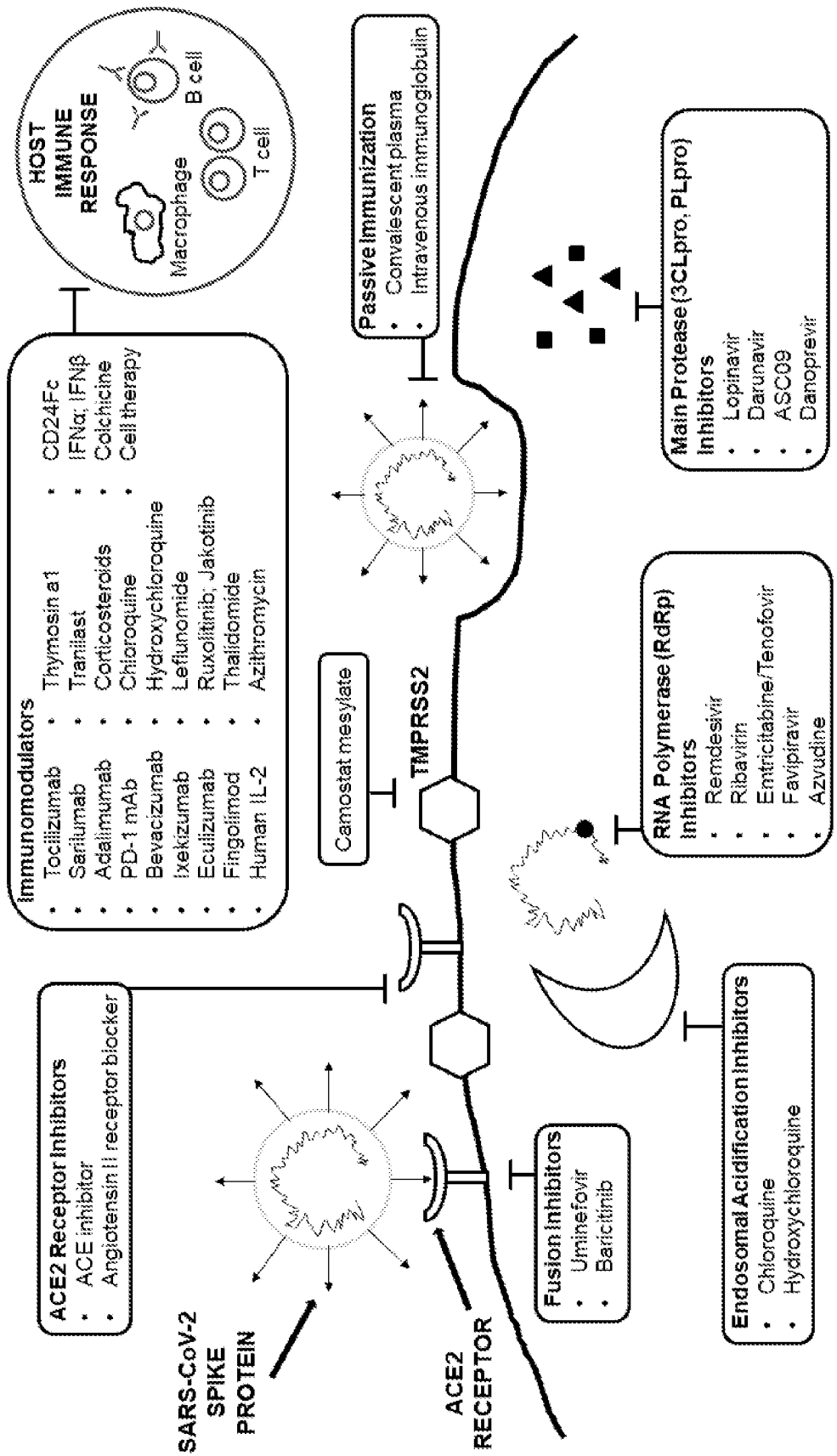
FIG. 1 shows the interaction of coronavirus with a host cell via the ACE2 receptor and various treatments for coronavirus.

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are those that are well known and commonly used in the art. In case of conflict, the present document, including definitions, will control. Preferred methods and materials are described below, although methods and materials similar or equivalent to those described herein can be used in practice or testing of the present invention.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. The term "about" as used herein refers to any values, including both integers and fractional components that are within a variation of up to +10% of the value modified by the term "about." In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, in some embodiments within 5-fold, and in some embodiments within 2-fold, of a value.

As used herein, the term "substantially" means to a significant extent, but not completely.

As used herein, all percentages (%) used for compositions or formulations refer to mass (or weight, w/w) percent unless noted otherwise.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

As used herein, the terms "administering," "providing" and "introducing" are used interchangeably herein and refer to the placement of the compositions of the disclosure into a subject by a method or route which results in at least partial localization of the composition to a desired site. The compositions can be administered by any appropriate route which results in delivery to a desired location in the subject.

As used herein, the terms "control," "reference level," and "reference" are used interchangeably and refer to a predetermined value or range, which is employed as a benchmark against which to assess the measured result. "Control group" as used herein refers to a group of control subjects. A control may be a subject, or a sample therefrom, whose disease state is known. The subject, or sample therefrom, may be healthy, diseased, diseased prior to treatment, diseased during treatment, or diseased after treatment, or a combination thereof.

The term "dose" as used herein denotes any form of the active ingredient formulation or composition that contains an amount sufficient to produce a therapeutic effect with at least a single administration. "Formulation" and "composition" are used interchangeably herein.

The term "dosage" as used herein refers to the administering of a specific amount, number, and frequency of doses over a specified period of time, typically one day.

As used herein, the terms "effective amount," "therapeutically effective amount," or "therapeutically effective rate(s)" refer to a substantially non-toxic, but sufficient amount or delivery rates of an agent or a composition or combination of compositions being administered that will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. It is understood that various biological factors may affect the ability of an agent to perform its intended task. Therefore, an "effective amount," "therapeutically effective amount," or "therapeutically effective rate(s)" may depend in some instances on such biological factors. For example, the precise determination of what would be considered an effective dose may be based on factors individual to each subject, including, but not limited to, the subject's age, size, type or extent of disease, stage of the disease, route of administration, the type or extent of supplemental therapy used, ongoing disease process and type of treatment desired (e.g., aggressive vs. conventional treatment). Further, while the achievement of therapeutic effects may be measured by a physician or a qualified medical practitioner using evaluations known in the art, it is recognized that individual variation and response to treatments may make the achievement of therapeutic effects a subjective decision. An appropriate "effective" amount in any individual case may be determined using techniques, such as a dose escalation study. The dose could be administered in one or more administrations. The determination of a therapeutically effective amount or delivery rate is well within the ordinary skill in the art of pharmaceutical sciences and medicine.

As used herein, "formulation" and "composition" can be used interchangeably and refer to a combination of at least two ingredients. In some embodiments, at least one ingredient may be an active agent or have properties that exert physiologic activity when administered to a subject.

As used herein, the terms "inhibit," "inhibition," or "inhibiting" refer to the reduction or suppression of a given condition, symptom, or disorder, or disease, or a significant decrease in the baseline activity of a biological activity or process.

As used herein, a subject is "in need of" a treatment if such subject would benefit biologically, medically, or in quality of life from such treatment.

As used herein, "treatment" or "treating" refers to means suppressing, repressing, reversing, alleviating, ameliorating, reducing the symptoms of, or inhibiting the progress of disease, or completely eliminating a disease. A treatment may be either performed in an acute or chronic way. The term also refers to reducing the severity of a disease or symptoms associated with such disease prior to affliction with the disease. Preventing the disease involves administering a composition or compound of the present invention to a subject prior to onset of the disease. Suppressing the disease involves administering a composition or compound of the present invention to a subject after induction of the disease but before its clinical appearance. Repressing or ameliorating the disease involves administering a composition or compound of the present invention to a subject after clinical appearance of the disease. In one embodiment, "treat," "treating," or "treatment" refers to alleviating or ameliorating at least one physical parameter including those which may not be discernible by the subject.

As used herein, the term "preventing" refers to a reduction in the frequency of, or delay in the onset of, symptoms of the condition or disease.

As used herein, the term "prophylaxis" refers to preventing or reducing the progression of a disorder, either to a statistically significant degree or as detectable to one skilled in the art. In one aspect as used herein, prophylaxis refers to the prevention of or reducing the incidence of recurrence of a cancer or tumor. In another aspect, prophylaxis refers to the prevention of or reducing the incidence of recurrence of viral infections, particularly, SARS-COV-2.

As used herein, "cancer" refers to diseases or disorders involving abnormal cell growth where the abnormal cells have the potential to invade or spread to other parts of the body (metastasis).

As used herein, "adenocarcinoma" refers to neoplasia of epithelial tissue that has a glandular origin, glandular characteristics, or combination thereof. Specific tissues affected by adenocarcinoma are lung, prostate, cervix, breast, pancreas, esophagus, stomach, colon, rectum, among others. Specific adenocarcinomas as used herein are infiltrating ductal adenocarcinoma, metastatic ductal adenocarcinoma, and neuroendocrine tumors.

As used herein, the terms "sample" or "test sample" refers any sample in which the presence and/or level of a target is to be detected or determined or any sample treated with the compositions as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a subject or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, the terms "subject" or "patient" interchangeably refer to any vertebrate, including, but not limited to, a mammal that is in need of a therapeutic treatment or prophylaxis described herein. The subject may be a human or a non-human. The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamsters, guinea pig, cat, dog, rat, and mouse. The mammal can be a primate such as a human. The subject may be of any age or stage of development, such as, for example, an adult, an adolescent, or an infant. The subject may be male. The subject may be female. In some embodiments, the subject may be undergoing other forms of treatment.

As used herein, the terms "therapeutic composition" and "pharmaceutical composition" can be used interchangeably and refer to a combination of at least two ingredients.

As used herein "stem cell" refers to an undifferentiated cell defined by its ability to self-renew and differentiate to produce progeny cells, including self-renewing progenitors, non-renewing progenitors, and terminally differentiated cells. Stem cells are characterized by their ability to differentiate into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; or (5) unipotent, meaning able to give rise to a single cell lineage (e.g., spermatogenic stem cells). Exemplary stem cells include embryonic stem cells, perinatal stem cells, adult stem cells, induced pluripotent stem cells, tissue-specific stem cells, mesenchymal stem cells, hematopoietic stem cells, mesenchymal stem cells, neural stem cells, or epithelial stem cells. In one aspect, the stem cell is a mesenchymal stem cell. In another aspect, the stem cell is an established line of mesenchymal stem cell. In another aspect, the stem cell is a subject-derived mesenchymal stem cell.

As used herein, the phrase "induced pluripotent stem cell (iPSC)" (or embryonic-like stem cell) refers to a proliferative and pluripotent stem cell which is obtained by de-differentiation of a somatic cell (e.g., an adult somatic cell).

As used herein "differentiation" refers to the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, "de-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Pharmaceutically acceptable salts of the compounds described herein are also contemplated for the uses described herein. As used herein, the terms "salt" or "salts" refer to an acid addition or base addition salt of a compound described herein. "Salts" include in particular "pharmaceutical acceptable salts." The term "pharmaceutically acceptable salts" refers to salts that retain the biological effectiveness and properties of the compounds disclosed herein and that typically are not biologically or otherwise undesirable. In many cases, the compounds disclosed herein can form acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine, and tromethamine.

Pharmaceutical excipients useful for the compositions as described herein comprise: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, ascorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, phosphate buffer saline); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); thickening agents (gelatin having a bloom strength of 50-100); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein. See *Remington's Essentials of Pharmaceutics*, Pharmaceutical Press Publishing Company, London, UK, 1st Edition, 2013, and the *Handbook of Pharmaceutical Excipients*, 8th Edition, Pharmaceutical Press Publishing Company London, U K, 2017, each of which is incorporated by reference herein for such teachings.

One embodiment described herein is a composition for treating or prophylaxis of a viral infection, particularly, SARS-COV-2. Another embodiment described herein is a composition for treating cancer, particularly adenocarcinomas, infiltrating ductal adenocarcinoma, metastatic ductal adenocarcinoma, and neuroendocrine tumors. In one embodiment, the composition comprises a combination of procaine, glutathione, DNase 1 (endonuclease 1), and RNase A. In one embodiment, the composition has the formulation shown in Table 1. In one embodiment, the composition is called TRESCELIUM™.

TABLE 1

Exemplary TRESCELIUM ™ Formulation

| Component | Concentration (mg/mL) | Concentration | Mass Percent (% mass/vol) |
|---|---|---|---|
| Procaine | ~0.13-0.2 | ~0.5-0.8 mM | ~0.013-0.02% |
| A tri- or tetra peptide comprising one or more glutamate residues | ~1.3-2.0 | ~4.3-6.5 mM | ~0.13-0.2% |
| DNase 1 | ~0.0008-0.0012 | ~0.02-0.04 µM | ~0.00008-0.00012% |
| RNase A* | ~0.008-0.012 | 0.0.6-0.8 µM | 0.0008-0.0012% |
| Solvent* (e.g., sterile water for injection) | | | |

*Optional components. An international unit (IU) of TRESCELIUM ™ is defined as 0.01 mL of the solution; 100 IU is 1 mL of the solution; 1000 IU is 10 ml of the solution Procaine, as used herein, refers to 2-(diethylamino) ethyl 4-aminobenzoate (MW: 236.31 g/mol) having the structure:

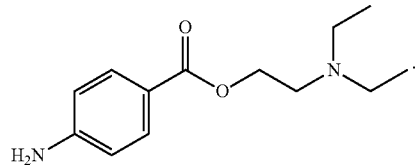 [SMILES: CCN(CC)CCOC(=O)c1ccc(N)cc1]

Procaine is supplied as a solution of 0.5 mg/ml (2.12 mM) (Bright Star Labs, LTD). Procaine inhibits ATP13A3, ATP5MG, ATP6AP1 (SIGMAR 1 complex) ion transportation. Without being bound by any theory, procaine is believed to bind to and inhibit voltage-gated sodium channels, thereby inhibiting the ionic flux of two electron transport system affected in SARS COV-2, specifically TRMT 1 and GPX1.

A tri- or tetra-peptide comprising one or more glutamate residues, as used herein, refers to a tri-peptide or tetra-peptide that contains one or more glutamic acid residues. In one aspect, the tri-peptide or tetra peptide comprises two or more glutamate residues. In another aspect, the tri-peptide or tetra-peptide comprises three or more glutamate residues. For example, E-E-X, X-E-E, E-X-E, E-E-X-X, E-E-X-E, E-X-E-E, X-E-E-E, or X-X-E-E, where E is a glutamate residue and X is any amino acid, and preferably an aliphatic amino acid. In one aspect, the tri-peptide comprises two glutamate residues and one aliphatic residue. In one aspect, the tetra peptide comprises two glutamate residues and two aliphatic residues, respectively. In another aspect, the tetra-peptide comprises three glutamate residues and one aliphatic residue. Non-limiting examples include: E-E-L, V-E-E, E-E-L-E, or E-E-I-V.

In one embodiment, the tri- or tetra-peptide comprising one or more glutamate residues is glutathione. Glutathione, as used herein, refers to $N^5$-(1-((carboxymethyl)amino)-3-mercapto-1-oxopropan-2-yl) glutamine (MW: 307.32 g/mol) having the structure:

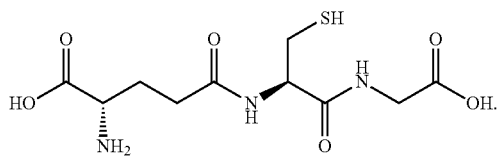 [SMILES: N[C@@H](CCC(=O)N[C@@H](CS)C(=O)NCC(=O)O)C(=O)O]

Glutathione is a tripeptide with a gamma peptide linkage between the carboxyl group of a glutamate side chain and cysteine. The carboxyl group of the cysteine residue is linked to glycine through a normal peptide bond. Glutathione is supplied as a solution of 5 mg/ml (16.2 mM) glutathione and 0.45 mg/mL NaCl (7.7 mM NaCl) (Proteo, Jalisco, MX). Without being bound by any theory, glutathione is believed to inhibiting binding of the SARS-COV-2 spike protein RBD with the host cell ACE2 receptor. Glutathione also has antioxidant activities.

Deoxyribonuclease I (DNase 1), as used herein, refers to human wild type deoxyribonuclease 1, human recombinant deoxyribonuclease 1, or bovine deoxyribonuclease 1. Other recombinant froms of DNase 1 from other organisms are within the scope of this disclosure and can be prepared using standard methods in the art. Specific human and bovine DNase 1 polypeptides have the amino acid sequences shown below.

```
Human DNase 1 (282 amino acids; 31433.73 Da)
                                        (SEQ ID NO: 1)
MRGMKLLGALLALAALLQGAVSLKIAAFNIQTFGETKMSNATLVSYIVQ
ILSRYDIALVQEVRDSHLTAVGKLLDNLNQDAPDTYHYVVSEPLGRNSY
KERYLFVYRPDQVSAVDSYYYDDGCEPCGNDTFNREPAIVRFFSRFTEV
REFAIVPLHAAPGDAVAEIDALYDVYLDVQEKWGLEDVMLMGDFNAGCS
YVRPSQWSSIRLWTSPTFQWLIPDSADTTATPTHCAYDRIVVAGMLLRG
AVVPDSALPENFQAAYGLSDQLAQAISDHYPVEVMLK Human Recombinant DNase 1
(260 amino acids; 29253.98 Da)
                                        (SEQ ID NO: 2)
LKIAAFNIQTFGETKMSNATLVSYIVQILSRYDIALVQEVRDSHLTAVG
KLLDNLNQDAPDTYHYVVSEPLGRNSYKERYLFVYRPDQVSAVDSYYYD
DGCEPCGNDTENREPAIVRFFSRFTEVREFAIVPLHAAPGDAVAEIDAL
YDVYLDVQEKWGLEDVMLMGDFNAGCSYVRPSQWSSIRLWTSPTFQWLI
PDSADTTATPTHCAYDRIVVAGMLLRGAVVPDSALPENFQAAYGLSDQL
AQAISDHYPVEVMLK Bovine DNase 1 (282 amino acids; 31345.52 Da)
                                        (SEQ ID NO: 3)
MRGTRLMGLLLALAGLLQLGLSLKIAAFNIRTFGETKMSNATLASYIVR
IVRRYDIVLIQEVRDSHLVAVGKLLDYLNQDDPNTYHYVVSEPLGRNSY
KERYLFLFRPNKVSVLDTYQYDDGCESCGNDSFSREPAVVKFSSHSTKV
KEFAIVALHSAPSDAVAEINSLYDVYLDVQQKWHLNDVMLMGDFNADCS
YVTSSQWSSIRLRTSSTFQWLIPDSADTTATSTNCAYDRIVVAGSLLQS
SVVPGSAAPFDFQAAYGLSNEMALAISDHYPVEVTLT
```

DNase 1 is supplied as a solution of 3 μg/mL (~0.01 μM) (Proteo, Jalisco, MX). COVID-19 subjects develop micro thrombosis where erythrocytes become lodged in capillaries and cause agglutination and inflammation. Without being bound by any theory, DNase 1 is believed to facilitate degradation of these complexes without eliciting a macrophage-induced cytokine storm. See e.g., Lee et al., Long-acting nanoparticulate DNase-1 for effective suppression of SARS-CoV-2-mediated neutrophil activities and cytokine storm," Biomaterials 267 (2021) 120389 (doi.org/10.1016/j.biomaterials.2020.120389). In one embodiment, DNase 1 is supplied in a composition containing both DNase 1 and RNase A (e.g., 3 μg/mL (4 UK/mL) bovine DNase A and 30 μg/mL (6 UK/mL) bovine RNase 1 (Proteo, Jalisco, MX).

In one embodiment, DNase can be PULMOZYMER (dornase alfa) inhalation solution (Genentech, Inc.). The Prescribing Information for PULMOZYMER (dornase alfa), revised January 2018, is incorporated by reference herein for such teachings.

As an optional component, Ribonuclease A (RNase 1), as used herein, refers to human wild type ribonuclease 1, recombinant human ribonuclease 1, bovine ribonuclease 1, or recombinant bovine ribonuclease 1. Natural human and bovine RNase A precursor polypeptides have the amino acid sequences shown below. Recombinant versions of active RNase A polypeptides from human, bovine, or other organisms and are within the scope of this disclosure and can be generated using standard methods in the art.

Human RNase A Precursor
(RNase 1, 156 amino acids - 128 in active form);
14574.3 Da)
(SEQ ID NO: 4)
*MALEKSLVRLLLLVLILLVLGWVQPSLG*KESRAKKFQRQHMDSDSSPSS
SSTYCNQMMRRRNMTQGRCKPVNTFVHEPLVDVQNVCFQEKVTCKNGQG
NCYKSNSSMHITDCRLTNGSRYPNCAYRTSPKERHIIVACEGSPYVPVH
FDASVEDST Bovine RNase A Precursor
(150 amino acids -124 in active form);
13562.1 Da)
(SEQ ID NO: 5)
*MALKSLVLLSLLVLVLLLVRVQPSLG*KETAAAKFERQHMDSSTSAASSS
NYCNQMMKSRNLTKDRCKPVNTFVHESLADVQAVCSQKNVACKNGQTNC
YQSYSTMSITDCRETGSSKYPNCAYKTTQANKHIIVACEGNPYVPVHFD
ASV
Italicized residues indicate precursor residues
that are removed in the active enzymes.

RNase A is supplied as a solution of 30 μg/mL (~2.2 μM) (Proteo, Jalisco, MX). COVID-19 subjects develop micro thrombosis where erythrocytes become lodged in capillaries and cause agglutination and inflammation. Without being bound by any theory, RNase A is believed to facilitate degradation of these complexes without eliciting a macrophage-induced cytokine storm. In one embodiment, RNase A is supplied in a composition containing both RNase A and DNase 1 (e.g., 3 μg/mL (4 UK/mL) bovine DNase A and 30 μg/mL (6 UK/mL) bovine RNase 1 (Proteo, Jalisco, MX).

In one embodiment, the composition described herein is created by combining sterile liquid formulations of the components in a 1:1:1 ratio of procaine, glutathione, and a mixture of DNase 1, and RNase A, i.e., 33.3% by volume of each solution. Commercially available solutions are shown in Table 2.

TABLE 2

Commercially available sterile solutions for preparing the composition

| Component | MW (g/mol) | mg/mL | Conc. (mM) | % mass/vol (g/mL) |
|---|---|---|---|---|
| Procaine | 236.31 | 0.5 | 2.1159 | 0.0500 |
| L-glutathione | 307.32 | 5.0 | 16.2697 | 0.5000 |
| DNase 1* | 31434 | 0.003 | 0.000095 | 0.0003 |
| RNase A*† | 13562 | 0.03 | 0.002212 | 0.0030 |

*Supplied together in single a solution of 3 μg/mL (4 UK/mL) bovine DNase A and 30 μg/mL (6 UK/mL) bovine RNase 1.
†RNase is an optional component of the composition.

In one embodiment, the composition comprises: about 9% by mass procaine or a pharmaceutically acceptable salt thereof; about 90% by mass glutathione or a pharmaceutically acceptable salt thereof; about 0.05% by mass DNase 1 or a pharmaceutically acceptable salt thereof; optionally about 0.55% by mass RNase A; and optionally, one or more pharmaceutically acceptable excipients.

The composition comprises about 5-15% by mass, including each integer within the specified range of procaine. The composition comprises about 85-95% by mass, including each integer within the specified range, of glutathione. The composition comprises about 0.01-0.1% by mass, including each integer within the specified range, of DNase 1. The composition comprises about 0.1-1.0% by mass, including each integer within the specified range, of RNase A.

The composition comprises about 0.13-0.20 mg/mL, about 0.15-0.18 mg/mL, or about 0.17 mg/mL, including each integer within the specified ranges of procaine. The composition comprises about 1.3-2.0 mg/mL, about 1.5-1.8 mg/mL, or about 1.7, including each integer within the specified ranges, of glutathione. The composition comprises about 0.0008-0.0012 mg/mL, about 0.0009-0.0011 mg/mL, or about 0.001 mg/mL, including each integer within the specified ranges, of DNase 1. The composition optionally comprises about 0.008-0.012 mg/mL, about 0.009-0.011 mg/mL, or about 0.01 mg/mL, including each integer within the specified ranges, of RNase A.

The composition comprises about 0.5-0.9 mM, about 0.6-0.8 mM, or about 0.7 mM, including each integer within the specified ranges of procaine. The composition comprises about 4.3-6.5 mM, about 5-6 mM, or about 5.4 mM, including each integer within the specified ranges, of glutathione. The composition comprises about 0.02-0.04 μM, about 0.025-0.035 M, or about 0.3 μM, including each integer within the specified ranges, of DNase 1. The composition optionally comprises about 0.5-0.9 μM, about 0.6-0.8 μM, or about 0.7 μM, including each integer within the specified ranges, of RNase A.

In one embodiment, the composition comprises the formulation as provided in Table 3.

TABLE 3

Exemplary TRESCELIUM ™ Composition

| Component | MW (g/mol) | mg/mL | Conc. (mM) | % m/v (g/mL) | % mass (w/w) |
|---|---|---|---|---|---|
| Procaine | 236.31 | 0.1667 | 0.7053 | 0.0167 | 9.04% |
| Glutathione | 307.32 | 1.6667 | 5.4232 | 0.1667 | 90.37% |
| DNase 1 | 31434 | 0.0010 | 0.000032 | 0.0001 | 0.05% |
| RNase A* | 13562 | 0.0100 | 0.000737 | 0.0010 | 0.54% |

*RNase A is an optional component of the composition.

As used herein "SARS-COV-2" is a beta-coronavirus (Beta-CoV or β-CoV). In particular, SARS-COV-2 is a Beta-CoV of lineage B. SARS-COV-2 may also be known as 2019 novel coronavirus or "2019-nCOV." Beta-coronaviruses are one of four genera of coronaviruses and are enveloped, positive-sense, single-stranded RNA viruses of zoonotic origin. Beta-coronaviruses mainly infect bats, but they also infect other species like humans, camels, and rabbits. SARS-COV-2 may be transferable between animals, such as between humans.

As used herein "viral transmission" is the process by which viruses spread between host subjects. Transmission occurs from person to person by direct or indirect contact or exposure. Examples of direct contact include, but are not limited to, the exchange of body fluids between a subject infected with the virus and someone else. Indirect contact includes, but is not limited to, exposure to bodily fluid droplets produced by a subject infected by the virus during coughing and/or sneezing. Beta-CoVs may induce fever and respiratory symptoms in humans. The overall structure of β-CoV genome contains an ORF1ab replicase polyprotein (rep, pp1ab) preceding other elements. This polyprotein is cleaved into many nonstructural proteins. SARS-COV-2 has a phenylalanine in the (F486) in the flexible loop of the receptor binding domain (RBD), flexible glycyl residues, and a four amino acid insertion ($R_{682}RAR_{685}$), called the polybasic clevage site, at the boundary between the S1 and S2 subunits that results in the introduction of a furin cleavage site. The furin cleavage site may result in SARS-COV-2 tissue tropism, increase transmissibility, and alter pathogenicity.

Diagnosis of SARS-COV-2 may comprise a positive test for SARS-COV-2 and/or onset of 2019-nCOV symptoms, or combinations thereof. Symptoms of SARS-COV-2 include, but are not limited to, one or more of the following symptoms: nasal congestion, sore throat, fever, body aches, exhaustion, dry cough, difficulty breathing, or a combination thereof. Subjects at higher risk of developing complications may be immunocompromised (e.g., undergoing cancer treatment, bone marrow or organ transplantation, immune deficiencies, poorly controlled HIV or AIDS, prolonged use of corticosteroids or immune weakening medications), have an underlying medical condition (e.g., diabetes, renal failure, liver disease), are pregnant, are at least 65 years of age, have a chronic lung disease, have a heart disease, or combinations thereof.

The composition described herein is useful for the treatment or prophylaxis of coronavirus infection by interfering with the SARS-COV-2 spike protein S1 receptor binding domain (RBD) interaction with the host cell angiotensin-converting enzyme 2 (ACE2) receptor. Without being bound by any theory, the composition complex is believed to alter the electrostatics of the SARS-CoV-2 S1 RBD interaction with the ACE2 receptor and inhibit binding, thus preventing viral spike protein-driven viral entry into cells. One embodiment described herein is a method for inhibiting the interaction of a SARS-COV-2 spike protein with a host cell ACE2 receptor, the method comprising contacting a SARS-COV-2 spike protein and/or a host cell ACE2 receptor with the TRESCELIUM™ composition described herein.

One of the symptoms of SARS COV-2 infection is a lowered oxygen concentration of in the blood. The Bohr-Haldane Effect regulates the transportation and exchange of respiratory gases in the blood, i.e., the process by which hemoglobin uptakes $O_2$ at the lungs and releases $O_2$ at the tissues, and conversely transports $CO_2$ from the tissues to the lungs. The Bohr-Haldane Effect and its biochemistry are well described in the medical literature. Without being bound by any theory, it is believed that TRESCELIUM™ activates this process, increasing the transfer of oxygen to the tissues in the body, and facilitating the release of oxygen and $CO_2$ from hemoglobin. Tests have shown that the level of oxygen in the blood increases dramatically and almost immediately after administrating TRESCELIUM™. As an example, the $SpO_2$ concentration of one COVID-19 infected subject increased from 74 to 83 in less than one minute after starting administration of TRESCELIUM™ via infusion. Similarly, another COVID-19 infected subject had a $SpO_2$ increase from 89 to 95 in less than 90 seconds after beginning administration of TRESCELIUM™ via infusion. One embodiment described herein is a method for increasing the $pO_2$ (or $SpO_2$) of a subject suffering from a respiratory ailment, the method comprising administering a therapeutically effective amount of the TRESCELIUM™ composition described herein.

In another embodiment, the composition described herein is used to treat, prophylaxis of, reducing the symptoms of, or prevent a viral infection, and particularly coronarius infections.

In another embodiment, the composition described herein is used to treat, reduce the symptoms of, prophylaxis of, or prevent asthma.

In another embodiment, the composition further comprises or is co-administered with one or more stem cells. The stem cells can be administered simultaneously, before, or after administration of the composition described herein. In one aspect, the stem cell comprises an embryonic stem cell, perinatal stem cell, adult stem cell, induced pluripotent stem cell, tissue-specific stem cell, mesenchymal stem cell, hematopoietic stem cell, mesenchymal stem cell, neural stem cell, or epithelial stem cell. In another aspect, the stem cell is a mesenchymal stem cell. In another aspect, the stem cell is a subject-derived stem cell.

The compositions described herein may be administered parenterally, orally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the composition described herein is administered intravenously. Sterile injectable forms of the composition described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. In one embodiment the composition is administered parenterally by injection, IV infusion, or by inhalation.

Pharmaceutically acceptable salts and deuterated variants can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and thereby reduce side effects.

Data obtained from cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular subject will depend upon a variety of factors, including the activity of the specific compound employed, the age, body weight, general health, gender, diet, time of administration, rate of excretion, drug combination, and the judgment of the treating physician and the severity of the particular disease being treated. The amount of a compound described herein in the composition will also depend upon the particular compound in the composition.

In one embodiment, the pharmaceutical compositions described herein provide a dosage form of the pharmaceutical compositions described here for administration to a subject. In one embodiment, the subject is suffering from or has the symptoms of a viral infection. In another embodiment, the subject is suffering from or has the symptoms of adenocarcinoma, infiltrating ductal adenocarcinoma, metastatic ductal adenocarcinoma, and neuroendocrine tumor. The dosage form can be administered, for example, to a subject, or a subject in need thereof. In one aspect, the subject is a mammal, or a mammal in need thereof. In one aspect, the subject is a human, or human in need thereof. In one aspect, the subject is a human or a human in need thereof. In one aspect, the subject is a child (~0-9 years old) or an adolescent (~10-17 years old). In one aspect, the subject is from about 0 to about 9 years of age. In another aspect, the subject is from about 10 years to about 17 years of age. In another aspect, the subject is over 17 years of age. In another aspect, the subject is an adult (≥18 years of age).

One or more dosage forms of the compositions described herein can be administered, for example, 1×, 2×, 3×, 4×, 5×, 6×, or even more times per day. One or more dosage forms can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to a viral infection or cancer.

In one embodiment, the compositions described herein can be administered as dosage forms in various regimens, including one dose per day (QD), two doses per day (BID), three doses per day (TID), or four times per day (QID) to achieve a total daily dosage. In another embodiment, any of the foregoing doses comprise a total daily dosage.

In one embodiment, for the treatment of a viral infection, 1000 IU of the composition described herein is administered intravenously on a daily basis until treatment is no longer required. In another embodiment, for prophylaxis of a viral infection, 100 IU of the composition described herein is administered intravenously on a daily basis until treatment is no longer required. In one aspect, the treatment or prophylaxis is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31, days. In another embodiment, the treatment or prophylaxis is administered for 1 week, 2, weeks, 3, weeks, 4, weeks, 5 weeks, 6, weeks, 7 weeks, 8 weeks, 9 weeks, or 10 weeks. In another embodiment, the treatment or prophylaxis is administered for 1 month, 2 months, 3 months, 4 months, 5 months, 6 months or even longer. In one embodiment treatment or prophylaxis is continued until no longer medically necessary to continue treatment.

Methods for treating, prophylaxis of, or ameliorating symptoms of a viral infection including administering an effective amount of the compositions detailed herein are contemplated. Methods for treating, prophylaxis of, or ameliorating symptoms of a viral infection or modulating a viral infection that includes administering an effective amount of the composition described herein.

Another embodiment described herein is a method of treating a subject suffering from, having the symptoms of, or at risk of contracting a viral infection by administering a composition describe herein, or pharmaceutically acceptable salts, hydrates, solvates, prodrugs, stereoisomers, or tautomers thereof, or combinations thereof, and optionally one or more pharmaceutically acceptable carriers. Another embodiment described herein is a method of treating a subject suffering from or having the symptoms of a viral infection by administering one or more of the pharmaceutical compositions described herein to the subject. The composition may be administered in one or more doses, one or more times per day for a total daily dosage. In one aspect, the compositions described herein are effective to at least partially treat, alleviate, prevent, or ameliorate symptoms of a viral infection. Further, provided herein are means for prophylaxis of or preventing a viral infection by administering to a subject an effective amount of the composition described herein.

For example, administration of the composition to the subject may result in inhibition or slowing of the viral infection. In another example, administration of the composition to the subject may result in inhibition or slowing of the normal rate of increase of viral load as compared to an untreated subject. As used herein, the term "viral load" is a measurement of the amount of a virus in a subject.

Another embodiment is a method of treating or preventing a viral infection in a subject in need thereof, the method comprising administering to the subject a therapeutically effective amount of a composition or formulation disclosed herein.

In another embodiment, the composition described herein is used to treat prophylaxis of, reducing the symptoms of, or prevent adenocarcinoma, infiltrating ductal adenocarcinoma, metastatic ductal adenocarcinoma, or neuroendocrine tumors.

In one embodiment, for the treatment of adenocarcinoma, infiltrating ductal adenocarcinoma, metastatic ductal adenocarcinoma, or neuroendocrine tumors, 1000 IU (10 mL) of the composition described herein is administered intravenously, by direct injection into the tumor, or combination thereof on a daily basis until treatment is no longer required or tumor size is reduced (e.g., to a size facilitating surgical removal). In one aspect, a portion of the dose is administered intravenously, and another portion is injected directly into the tumor. The ratio of the intravenous dose to the direct injection dose can be: 90:10, 80:20, 70:30, 60:40, 50:50, 40:60, 30:70, 20:80, or 10:90. In one aspect, the ratio of the intravenous dose to the direct injection dose is 70:30. In one aspect, 7 mL are administered intravenously and 3 mL are injected directly into the tumor.

In another embodiment, for prophylaxis of recurrence of adenocarcinoma, infiltrating ductal adenocarcinoma, metastatic ductal adenocarcinoma, and neuroendocrine tumor, 1000 IU (10 mL) of the composition described herein is administered intravenously or by injection on a daily basis, weekly basis, monthly basis, or combinations thereof until treatment is no longer required. In one aspect, the treatment or prophylaxis is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31, days. In another embodiment, the treatment or prophylaxis is administered for 1 week, 2, weeks, 3, weeks, 4, weeks, 5 weeks, 6, weeks, 7 weeks, 8 weeks, 9 weeks, 10 weeks, 12 weeks, 15 weeks, 20 weeks, 30 weeks, 40 weeks, 50 weeks, or even longer. In another embodiment, the treatment or prophylaxis is administered for 1 month, 2 months, 3 months, 4 months, 5 months, 6 months, 7 months, 8 months, 9 months, 10 months, 11 months, 12 months, or even longer. In another embodiment, the treatment or prophylaxis is administered for 1 year, 2 years, 3 years, 4 year, 5 years, over 5 years, or even longer. In one embodiment treatment or prophylaxis is continued until no longer medically necessary to continue treatment.

Another embodiment described herein is a dosing regimen for treating adenocarcinoma, infiltrating ductal adenocarcinoma, metastatic ductal adenocarcinoma, or neuroendocrine tumors. In one aspect, 1000 IU (10 mL) of the composition described herein is administered intravenously, by direct injection into the tumor, or combination thereof on a daily basis until treatment is no longer required or tumor size is reduced (e.g., to a size facilitating surgical removal). In one aspect, a portion of the dose is administered intravenously, and another portion is injected directly into the tumor. The ratio of the intravenous dose to the direct injection dose can be: 90:10, 80:20, 70:30, 60:40, 50:50, 40:60, 30:70, 20:80, or 10:90. In one aspect, the ratio of the intravenous dose to the direct injection dose is 70:30. In one aspect, 7 mL are administered intravenously and 3 mL are injected directly into the tumor. The treatment is continued on a daily basis until the tumor size is reduced to a level that it can be surgically removed. During surgery or shortly thereafter, the composition (2-10 mL) is administered directly into the tissue where the tumor existed. About two weeks after removal of the tumor (ca. 15 days) a prophylactic treatment phase begins. The composition described herein is administered daily at a dose of 1000 IU (10 mL) of intravenously and direct injection into the tissue area where the tumor was removed at a ratio of the intravenous dose to the direct injection dose of 70:30 (7 mL intravenously; 3 mL direct injection). This phase is continued on a daily basis for 2 to 3 months (60 to 90 days). After the initial prophylactic treatment phase, the composition is administered once per week in the same manner (1000 IU (10 mL) at a ratio of 70:30 intravenous to direct injection). This weekly prophylactic administration phase is continued for at least 3 months and up to 6 months or longer. Treatment efficacy and cancer reoccurrence is monitored by standard techniques including digital palpation, X-ray, PET scans, and MRI scans. Treatment may be reinitiated if a tumor reoccurs.

Methods for treating, prophylaxis of, or ameliorating symptoms of adenocarcinoma, infiltrating ductal adenocarcinoma, metastatic ductal adenocarcinoma, and neuroendocrine tumor, including administering an effective amount of the compositions detailed herein are contemplated. Methods for treating, prophylaxis of, or ameliorating symptoms of adenocarcinoma, infiltrating ductal adenocarcinoma, metastatic ductal adenocarcinoma, and neuroendocrine tumor, that includes administering an effective amount of the composition described herein.

Another embodiment described herein is a method of treating a subject suffering from, having the symptoms of or prophylaxis of the recurrence of adenocarcinoma, infiltrating ductal adenocarcinoma, metastatic ductal adenocarcinoma, and neuroendocrine tumor, by administering a composition describe herein, or pharmaceutically acceptable salts, hydrates, solvates, prodrugs, stereoisomers, or tautomers thereof, or combinations thereof, and optionally one or more pharmaceutically acceptable carriers. Another embodiment described herein is a method of treating a subject suffering from or having the symptoms of adenocarcinoma, infiltrating ductal adenocarcinoma, metastatic ductal adenocarcinoma, or neuroendocrine tumor by administering one or more of the pharmaceutical compositions described herein to the subject. The composition may be administered in one or more doses, one or more times per day for a total daily dosage. In one aspect, the compositions described herein are effective to at least partially treat, alleviate, prevent, or ameliorate symptoms of adenocarcinoma, infiltrating ductal adenocarcinoma, metastatic ductal adenocarcinoma, or neuroendocrine tumor. Further, provided herein are means for prophylaxis of or preventing adenocarcinoma, infiltrating ductal adenocarcinoma, metastatic ductal adenocarcinoma, or neuroendocrine tumor by administering to a subject an effective amount of the composition described herein.

For example, administration of the composition to the subject may result in inhibition of growth or cytoreduction of the adenocarcinoma, infiltrating ductal adenocarcinoma, metastatic ductal adenocarcinoma, or neuroendocrine tumor. Administration of the composition to the subject may result in an inhibition of the tumor growth rate. In another aspect, administration of the composition to the subject may result in a reduction in the tumor size, which may facilitate surgical removal or treatment with radiation or chemotherapeutics.

Another embodiment is a method of treating adenocarcinoma or preventing the reoccurrence of adenocarcinoma in a subject in need thereof, the method comprising administering to the subject a therapeutically effective amount of a composition or formulation disclosed herein at a dosing regimen as disclosed herein. In one aspect, the treatment may be combined with chemotherapeutics, radiation, or a combination thereof.

Another embodiment is a method of manufacturing a composition comprising combining procaine, glutathione, DNase 1, and optionally RNase A; and filing the composition into receptacles for storage or administration.

Another embodiment is a method for manufacturing a dosage form comprising formulating a composition as described herein comprising sprays, capsules, tablets, elixirs, emulsions, lozenges, suspensions, syrups, pills, lotions, epidermal patches, suppositories, inhalers, or injectables. Any methods known to the art for formulating the active principal ingredients into a pharmaceutically acceptable composition may be utilized. In some embodiments, the composition may be in the form of an injectable solution. In some embodiments, the composition may be in the form of an inhalable composition.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All the various embodiments, aspects, and options disclosed herein can be combined in any variations or iterations. The scope of the compositions, formulations, methods, and processes described herein include all actual or potential combinations of embodiments, aspects, options, examples, and preferences herein described. The compositions, formulations, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the specification discloses and describes merely exemplary embodiments. All patents and publications cited herein are incorporated by reference herein for the specific teachings thereof.

Various embodiments and aspects of the inventions described herein are summarized by the following clauses:

Clause 1. A pharmaceutical composition comprising:
procaine or a pharmaceutically acceptable salt thereof;
a tri- or tetra-peptide comprising one or more glutamate residues or a pharmaceutically acceptable salt thereof;
DNase 1 or a pharmaceutically acceptable salt thereof.

Clause 2. The composition of clause 1, wherein the composition further comprises RNase A, or a pharmaceutically acceptable salt thereof.

Clause 3. The composition of clause 1 or 2, wherein the composition further comprises one or more pharmaceutically acceptable excipients.

Clause 4. The composition of any one of clauses 1-3, wherein the composition comprises:
about 5-15% by mass procaine or a pharmaceutically acceptable salt thereof;
about 85-95% by mass of a tri- or tetra-peptide comprising one or more glutamate residues or a pharmaceutically acceptable salt thereof;
about 0.01-0.1% by mass DNase 1 or a pharmaceutically acceptable salt thereof;

Clause 5. The composition of any one of clauses 1-4, wherein the composition comprises:
about 8-10% by mass procaine or a pharmaceutically acceptable salt thereof;
about 88-92% by mass of a tri- or tetra-peptide comprising one or more glutamate residues or a pharmaceutically acceptable salt thereof; and
about 0.02-0.08% by mass DNase 1 or a pharmaceutically acceptable salt thereof.

Clause 6. The composition of any one of clauses 1-5, wherein the composition comprises:
about 9% by mass procaine or a pharmaceutically acceptable salt thereof;
about 90% by mass of a tri- or tetra-peptide comprising one or more glutamate residues or a pharmaceutically acceptable salt thereof; and
about 0.05% by mass DNase 1 or a pharmaceutically acceptable salt thereof.

Clause 7. The composition of any one of clauses 1-6, wherein the composition further comprises about 0.5% by mass RNase A or a pharmaceutically acceptable salt thereof.

Clause 8. The composition of any one of clauses 1-7, wherein the composition comprises about 0.1-0.3 mg/mL procaine; about 1-3 mg/ml of a tri- or tetra-peptide comprising one or more glutamate residues; and about 0.0008-0.0012 mg/mL DNase 1.

Clause 9. The composition of any one of clauses 1-8, wherein the composition comprises about 0.2 mg/mL procaine; about 2 mg/ml of a tri- or tetra-peptide comprising one or more glutamate residues; and about 0.001 mg/mL DNase 1.

Clause 10. The composition of any one of clauses 1-9, wherein the composition further comprises and about 0.01 mg/mL by mass RNase A.

Clause 11. The composition of any one of clauses 1-10, wherein the tri- or tetra-peptide comprising one or more glutamate residues comprises glutathione, E-E-X, X-E-E, E-X-E, E-E-X-X, E-E-X-E, E-X-E-E, E-X-X-E, X-E-E-E, or X-X-E-E, wherein E is a glutamate residue and X is any amino acid, and preferably an aliphatic amino acid.

Clause 12. The composition of any one of clauses 1-11, wherein the tri- or tetra-peptide comprising one or more glutamate residues comprises glutathione (γE-C-G)

Clause 13. The composition of any one of clauses 1-12, wherein the composition comprises: 9.0% by mass procaine; 90.4% by mass glutathione; and 0.05% by mass DNase 1.

Clause 14. The composition of any one of clauses 1-13, wherein the composition comprises: 0.17 mg/mL procaine (0.71 mM); 1.7 mg/mL glutathione (5.4 mM); 0.001 mg/ml (0.3 μM) DNase 1.

Clause 15. The composition of any one of clauses 1-14, wherein the composition is a liquid suitable for injection or inhalation.

Clause 16. The composition of any one of clauses 1-15, wherein the composition further comprises or is co-administered with one or more stem cells.

Clause 17. The composition of clause 16, wherein the stem cell is an embryonic stem cell, perinatal stem cell, adult stem cell, induced pluripotent stem cell, tissue-specific stem cell, mesenchymal stem cell, hematopoietic stem cell, mesenchymal stem cell, neural stem cell, or epithelial stem cell.

Clause 18. The composition of clause 16, wherein the stem cell is a mesenchymal stem cell.

Clause 19. The composition of clause 16, wherein the stem cell is a subject-derived stem cell.

Clause 20. A method or means for treating, reducing the symptoms of, or prophylaxis of a viral infection, the method comprising administering a therapeutically effective amount to a subject in need thereof of a composition comprising procaine or a pharmaceutically acceptable salt thereof; glutathione a pharmaceutically acceptable salt thereof; and DNase 1 or a pharmaceutically acceptable salt thereof.

Clause 21. The method of clause 20, wherein the viral infection is a coronavirus or a respiratory virus.

Clause 22. The method of clause 20 or 21, wherein the viral infection is SARS-COV-2.

Clause 23. The method of any one of clauses 20-22, wherein 1000 IU (10 mL) per day of the composition are administered to the subject in need thereof as a treatment.

Clause 24. The method of any one of clauses 20-23, wherein 100 IU (1 mL) per day of the composition are administered to the subject in need thereof as a prophylactic.

Clause 25. The method of any one of clauses 20-24, wherein the therapeutically effective amount of the composition is administered daily for 1 to 60 days.

Clause 26. The method of any one of clauses 20-25, wherein the therapeutically effective amount of the composition is administered by injection, infusion, or inhalation.

Clause 27. The method of any one of clauses 20-26, wherein the therapeutically effective amount of the composition is administered as a dosage regimen comprising one dose per day (QD), two doses per day (BID), three doses per day (TID), or four doses per day (QID) to achieve a total daily dosage.

Clause 28. Use of the composition of any one of clauses 1-19 as a medicament for treating, reducing the symptoms of, or prophylaxis of a viral infection.

Clause 29. A method for increasing the $SpO_2$ of a subject suffering from a respiratory virus infection, the method comprising administering a therapeutically effective dose of a composition comprising procaine or a pharmaceutically acceptable salt thereof; glutathione a pharmaceutically acceptable salt thereof; and DNase 1 or a pharmaceutically acceptable salt thereof.

Clause 30. A method for manufacturing a pharmaceutical composition, the method comprising:
  combining procaine, a tri- or tetra-peptide comprising one or more glutamate residues, DNase 1; and
  filing the pharmaceutical composition into a receptacle for storage or administration.

Clause 31. A pharmaceutical composition produced by the method of clause 30.

Clause 32. A method for treating adenocarcinoma or prophylaxis of recurrence thereof, the method comprising administering a therapeutically effective amount to a subject in need thereof of a composition comprising procaine or a pharmaceutically acceptable salt thereof; glutathione a pharmaceutically acceptable salt thereof; and DNase 1 or a pharmaceutically acceptable salt thereof.

Clause 33. The method of clause 32, wherein the adenocarcinoma is infiltrating ductal adenocarcinoma, metastatic ductal adenocarcinoma, or neuroendocrine tumors.

Clause 34. The method of clause 32 or 33, wherein the adenocarcinoma is infiltrating ductal adenocarcinoma.

Clause 35. The method of any one of clauses 32-34, wherein a dose of 1000 IU (10 mL) per day of the composition is administered to the subject in need thereof as a treatment.

Clause 36. The method of any one of clauses 32-35, wherein the treatment is administered daily for 1 to 180 days.

Clause 37. The method of any one of clauses 32-36, wherein the treatment is administered by administering a portion of the dose intravenously and a portion of the dose is injected directly into an adenocarcinoma tumor.

Clause 38. The method of any one of clauses 32-37, wherein 70% of the dose is administered intravenously and 30% of the dose is injected directly into the adenocarcinoma tumor.

Clause 39. The method of any one of clauses 32-38, wherein the treatment is administered until a size of the adenocarcinoma tumor is reduced.

Clause 40. The method of any one of clauses 32-39, wherein the treatment is combined with a chemotherapeutic agent, radiation, or a combination thereof.

Clause 41. The method of any one of clauses 32-40, wherein the adenocarcinoma tumor is surgically removed following a reduction of size.

Clause 42. The method of any one of clauses 32-41, wherein a dose of 1000 IU (10 mL) per day or per week of the composition is administered to the subject in need thereof as a prophylactic.

Clause 43. The method of any one of clauses 32-42, wherein the dose is administered daily for 30 days to 180 days.

Clause 44. The method of any one of clauses 32-43, wherein the dose is administered weekly for 1 week to 52 weeks.

Clause 45. The method of any one of clauses 32-44, wherein the dose is administered monthly for 1 month to 48 months.

Clause 46. Use of the composition of any one of clauses 1-19 as a medicament for treating adenocarcinoma or prophylaxis of recurrence thereof.

Clause 47. A method for inhibiting growth or causing cytoreduction of an adenocarcinoma, the method comprising contacting an adenocarcinoma with the composition of any one of clauses 1-19.

EXAMPLES

Example 1

The TRESCELIUM™ composition is prepared by combining procaine, glutathione, DNase 1, and RNase A as a sterile solution suitable for intravenous administration. A ratio of 1:1:1 of each of three sterile solutions of procaine, glutathione, and DNase 1/RNase A are mixed to form a solution having the concentrations shown in Table 4.

TABLE 4

Exemplary TRESCELIUM ™ Composition

| Component | mg/mL | Conc. (mM) | % m/v (g/mL) | % mass (w/w) |
|---|---|---|---|---|
| Procaine | 0.1667 | 0.7053 | 0.0167 | 9.04% |
| Glutathione | 1.6667 | 5.4232 | 0.1667 | 90.37% |
| DNase 1* | 0.0010 | 0.000032 | 0.0001 | 0.05% |
| RNase A*† | 0.0100 | 0.000737 | 0.0010 | 0.54% |

*Supplied together in single a solution.
†RNase is optional in the composition.
An international unit (IU) of TRESCELIUM ™ is defined as 0.01 mL of the solution; 100 IU is 1 mL of the solution; 1000 IU is 10 mL of the solution.

TRESCELIUM™ is a slightly yellow/crystalline liquid prepared for intravenous administration in a vial. An intravenous injection or infusion of 100 international units (IU) (1 mL) is administered daily as a prophylactic dose. An intravenous injection or infusion of 1000 international units (IU) (10 mL) is administered daily as a therapeutic dose.

TRESCELIUM™ molecular complex alters the electrostatics of Subunit 1 of the receptor-binding domain (RBD) region in the spike protein of the SARS-COV-2 which diminishes the interaction of the spike protein RBD with the host cell ACE2 receptor.

TRESCELIUM™ molecular complex interacts with para-aminobenzoic acid (PABA) and dimethylaminoethanol (DMAE) to increase the production of phosphatidylcholine which in turn increases the adsorption of oxygen in a cell.

Cancer cells typically grow in an anaerobic environment. Since TRESCELIUM™ promotes the absorption of oxygen, it is believed to inhibit the growth of the cancer cells. As a result, the tumor shrunk significantly (cytoreduction) facilitating surgical removal.

Example 2

The TRESCELIUM™ composition described herein has been administered under compassionate use to approximately 2,000 individuals infected with SARS-COV-2 (COVID-19) in Mexico under compassionate use protocols. As a treatment for individuals infected with the virus, 1000 IU/day were administered intravenously. As a prophylactic, 100 IU/day were administered. Nearly 100% of infected subjects recovered following treatment. The prophylactic treatment has prevented nearly 100% of individuals from contracting the SARS-COV-2 virus.

Example 3

The TRESCELIUM™ composition described herein has been administered under compassionate use to cancer subjects in Mexico as described:

Subject 1: Invasive Ductal Carcinoma, Mucinous Type

A 78-year-old female subject with 12.0 cm tumor on right breast. The subject was not a candidate for mastectomy, radiotherapy, or chemotherapy.

TRESCELIUM™ was used as a compassionate treatment. A dose of 10 mL was injected daily for 30 days, 70% intravenous and 30% directly in the tumor area for 28 days until the tumor reduced to 5.4 cm (approximately 50%). At this point the tumor was surgically removed (Sep. 11, 2014). TRESCELIUM™ was administered to the void where the tumor was removed.

Fifteen days after removal of the tumor, phase 2 was initiated. TRESCELIUM™ was administered daily for 30 days at a dose of 10 mL, 70% intravenous and 30% directly in the area where the tumor was removed. After 30 days, TRESCELIUM™ was administered every 3 days for 90 days. After the 90-day period (135 days after surgery), TRESCELIUM™ was administered weekly for 6.5 months. PET scans showed no evidence of recurring cancer.

After four years, a 1.5 cm tumor was identified in the same area of the right breast. Treatment with TRESCELIUM™ was reinitiated (daily 10 ml dose; 70% intravenous and 30% directly in the tumor). A mastectomy was performed 15 days after the treatment was restarted. Treatment with TRESCELIUM™ was continued as described above for one year with no relapses or metastases.

Subject 2: Invasive Ductal Carcinoma

A 61-year-old female subject with 7.0 cm tumor on left breast. The subject was not a candidate for a mastectomy, radiotherapy, or chemotherapy.

TRESCELIUM™ was used as a compassionate treatment. A dose of 10 mL was injected daily for 30 days, 70% intravenous and 30% directly in the tumor area. After 30 days the tumor was reduced by approximately 50%. At this point the tumor was removed (Oct. 13, 2016). TRESCELIUM™ was administered to the void where the tumor was removed.

Fifteen days after removal of the tumor, phase 2 was initiated. TRESCELIUM™ was administered daily for 30 days at a dose of 10 mL, 70% intravenous and 30% directly in the area where the tumor was removed. After 30 days, TRESCELIUM™ was administered every 3 days for 90 days. After the 90-day period (135 days after surgery), TRESCELIUM™ was administered weekly for 10 weeks. At six months after starting treatment, PET scans showed no evidence of recurring cancer.

After 2 years (2019), a similar tumor was discovered at the same location and was surgically removed.

Example 4

Evaluation of TRESCELIUM™ Toxicity on Newborn Piglets.

The purpose of this study is to test the toxicity of TRESCELIUM™ in newborn piglets and to verify alternate responses in metabolic function, tissue development, maintenance and growth for use and productive purposes. A secondary objective is to improve the health conditions of treated piglets, as the TRESCELIUM™ will initially be applied to a group of piglets that have less favorable conditions compared to the control group.

The experimental applications were performed by a licensed veterinarian in Mexico. The first administration was given to newborn piglets weighting between 1.5 and 2 kg. A second administration at a 10-fold higher does was performed when the piglets were in the pre-weening stage and weighed between 3 and 6 kg. Another 40 piglets were selected as a control group for comparing factors such as mortality rate, weight gain, appetite, and overall development for 15 days.

The 40 piglets selected for the Test Group were considered to have lower productive capacity that the piglets in the Control Group.

Number of piglets in Test Group: 40 piglets
Number of piglets in Control Group: 40 piglets
Quantity of TRESCELIUM™ administered to each piglet:
Experiment 1:10 mL for every 1.6 kg of weight
Experiment 2:0.32 mL for every 1.6 kg of weight
Route of administration: Intramuscular injection
Administration of a First Dose of TRESCELIUM™

A dose of 0.10 mL of TRESCELIUM™ was administered to 40 piglets each with an average weight of 1.6 kg (e.g., a recommended dose based on weight) and the following results shown in Table 5 were observed.

TABLE 5

Piglet Toxicity with a Single 0.1 mL Dose of TRESCELIUM ™

| Test Group: 0.1 mL TRESCELIUM ™ via IM | Control Group |
|---|---|
| No negative reactions | No negative reactions |
| Appetite: Stable | Appetite: Stable |
| Mortality: 1 out of 40 (2.5%) | Mortality: 4 out of 40 (10%) |
| Death Reason: Congenital alteration: Leg abduction syndrome | Death Reason: Various reasons related to feeding |

Administration of a Second Dose of TRESCELIUM™

A second dose of 1.0 mL was administered to 40 piglets with an average weight of 5.5 kg (dose increased by 333% based on weight) and the following results shown in Table 6 were observed.

TABLE 6

Piglet Toxicity with a Second 1.0 mL Dose of TRESCELIUM ™

| Test Group: 1.0 mL TRESCELIUM ™ via IM | Control Group |
|---|---|
| No negative reactions | No negative reactions |
| Appetite: Stable | Appetite: Stable |
| Development and weight: Uniform optimal weights within the upper margin of the average | Development and weight: Growth and development was less uniform, weights within the lower and below-average limits |
| Additional Mortality: 0% | Additional Mortality: 0% |
| Death Reason: N/A | Death Reason: N/A |

General Conclusions

No indication of toxicity was identified in the group exposed to treatment at the birth stage and no adverse effects were manifested that would affect the overall development of the animal.

The mortality rate was reduced from 10.0% to 2.5%. The Test group also presented uniformly with improvements in appetite and weight as compared to the Control Group.

Example 5

Clinical Study: Safety and Efficacy of TRESCELIUM™ Treatment

For diagnosis of COVID-19, the tests most utilized include Reverse Transcription Polymerase Chain Reaction (RT-PCR), Immunoassay using Enzyme-Linked Immunosorbent Assay (ELISA), and Computed Tomography scan (CT scan). For prevention of COVID-19 transmission, most of the actions involve social distancing, but also include the development of new vaccines and the use of drug re-purposing as important pharmacological interventions.

One of the first drugs used as both a preventive and treatment approach for COVID-19 was hydroxychloroquine, which has shown no effective results and has a reported side effect rate of 40.1%. Studies with other drugs like RNA-dependent RNA polymerase (RdRp) enzyme inhibitors, protease inhibitors, interferons, antibodies, convalescent plasma, and corticosteroids still have no conclusive data or enough positive results. To this day, mRNA vaccines are the most effective and secure COVID-19 prevention option, but data on vaccine efficacy in people previously infected with COVID-19 or people who are immunocompromised are still limited. Furthermore, each vaccine is more or less effective depending on the specific virus strain.

The compound TRESCELIUM™ dramatically increases oxygenation in subjects with Severe Acute Respiratory Syndrome (SARS). This property should significantly reduce the mortality of individuals suffering from SARS associated with COVID-19 infection. The primary objectives of this study were to determine the efficacy and safety of TRESCELIUM™ as a preventive medication for COVID-19 using a 5 cc (5 mL) IV dose, and to determine the efficacy and safety of TRESCELIUM™ as a treatment medication for COVID-19 using one or more applications of a 10 cc IV dose. The secondary objective was to identify any potential side effects that can result from administration of TRESCELIUM™.

The study lasted 12 months from Mar. 3, 2020, to Feb. 28, 2021. Because the study started as a compassionate treatment option, no sampling was done. All subjects that applied and requested TRESCELIUM™ were treated. The preventive treatment consisted of one unique IV dose of 5 cc TRESCELIUM™. Treatment for subjects infected with or showing symptoms of COVID-19 included one or more applications of 10 cc (10 mL) TRESCELIUM™. Most subjects presented a significant recovery after a single dose of TRESCELIUM™. Severe or critically ill subjects that did not show an improvement after 12 hours were given a second dose. In very few instances, subjects that did not show a clear improvement had additional doses administered on demand every 12 hours. No control or comparative studies were performed in this study. Subjects were treated individually or assembled into groups for treatment. The time of application varied. Subjects were free to withdraw from the study at any time without giving a reason. Subjects were advised that if they requested to withdraw from the study at any time, there would be no negative consequences.

The study consisted of the following steps: group assignation; identification and personal information collected of subjects; treatment administration start; treatment administration end; two-month follow-up; data preparation; data analysis; and report writing (Table 7).

TABLE 7

Examinations and Procedure Steps for the TRESCELIUM ™ Study

| Step | Study Day |
|---|---|
| Group assignation | 1 |
| Identification and personal information | 1 |
| Treatment administration starts | 14 |
| Treatment administration ends | 360 |
| Follow-up ends | 420 |
| Data preparation | 480 |
| Data analysis | 480 |
| Report writing | 520 |

This study was conducted at the following locations in Mexico: Aguascalientes, Aguascalientes; Apatzingán, Michoacán; Cancún, Quintana Roo; Chiapas; Ciudad Cuauhtémoc, Chihuahua; Ciudad Guzmán, Jalisco; Ciudad de México; Ciudad Juárez, Chihuahua; Ciudad Obregón, Sonora; Culiacán, Sinaloa; Empalme, Sonora; Guadalajara, Jalisco; Guasave, Sinaloa; Hermosillo, Sonora; Huatabampo, Sonora; León, Guanajuato; Los Cabos, Baja California Sur; Los Mochis, Sinaloa; Mazatlán, Sinaloa; Monterrey, Nuevo León; Navojoa, Sonora; Ocotlán, Jalisco; Puebla, Puebla; Tecomán, Colima; Tijuana, Baja California Norte; Tuxpan, Nayarit; Villa Unión, Sinaloa; Zamora, Michoacán; Zapopan, Jalisco; and Zapotiltic, Jalisco.

In this study, the total subject pool was divided into two groups: Group One (1,060 subjects that did not pay for the treatment) and Group Two (404 subjects that paid for the treatment). Individuals were designated as "infected" or "COVID-19 positive" based on a positive PCR test, $SpO_2$ levels lower than 95%, a combination of reduced $SpO_2$ levels and other symptoms associated with the virus, or clinically diagnosable infection. $SpO_2$ is a measure of the amount of oxygen-carrying hemoglobin in the blood relative to the amount of hemoglobin not carrying oxygen. The severity of reduced $SpO_2$ levels is defined as: Mild (over 95% $SpO_2$); Moderate (between 93-94% $SpO_2$); Serious (between 90-92% $SpO_2$); Severe (between 85% to 89% $SpO_2$); and Critical (below 85% $SpO_2$). Data of pre-existing conditions were collected from the subjects.

Some subjects were also receiving treatment for diabetes, heart disease, asthma, etc. However, this data was not analyzed in this study. Additionally, there was no randomization or sampling of subjects in this study.

All subjects in the study were administered TRESCELIUM™. TRESCELIUM™ is composed of a combination of three components, each part of which has been deemed safe either implicitly or explicitly for human use and is delivered as a solution by IV injection. TRESCELIUM™ efficacy is understood as a reduction of positive symptoms of COVID-19. TRESCELIUM™ safety is understood as minimum serious side effects when administered as a preventive or as a treatment for COVID-19. The efficacy and safety measurements assessed included two parameters: subjects that were infected with COVID-19 and subjects that had adverse reactions after receiving IV injections of TRESCELIUM™.

A total of 1,464 subjects were treated with TRESCELIUM™. The total number of subjects in the preventive group was 1,071, while the total number of subjects in the treatment group was 393. Data analysis consisted of descriptive statistics for subjects that were infected. The details of distribution, treatment, and withdrawal for the study are presented below in Table 8.

TABLE 8

Disposition of subjects in the TRESCELIUM ™ study

| | Group One (N = 1060) | Group Two (N = 404) | Total (N = 1464) |
|---|---|---|---|
| Enrolled | 1060 | 404 | 1464 |
| Preventive-received one injection | 981 | 90 | 1071 |
| Treatment-received at least one injection | 79 | 314 | 393 |
| Withdrawn | 0 | 0 | 0 |
| Adverse event | 42 | 28 | 70 |
| Death by COVID | 2 | 4 | 6 |
| Death by other comorbidities | 5 | 0 | 5 |

Efficacy Results

In Group One, 1,060 subjects were treated with TRESCELIUM™. A total of 79 subjects were administered TRESCELIUM™ as a treatment, while 981 subjects were administered TRESCELIUM™ as a preventive therapy. Of the 79 subjects that were infected with COVID-19 before receiving TRESCELIUM™, 66 subjects (83.54%) recovered after one dose of TRESCELIUM™. Thirteen subjects (16.46%) required additional doses of TRESCELIUM™, and all recovered. Of the 981 subjects that were dosed with TRESCELIUM™ on a preventive basis, 950 subjects (96.84%) did not develop any symptoms of COVID-19. Thirty-one subjects developed symptoms and required additional doses of TRESCELIUM™. Twenty-nine of the 31 subjects ultimately recovered; two did not survived.

In Group Two, 404 subjects were treated with TRESCELIUM™. A total of 314 subjects were administered TRESCELIUM™ as a treatment, while 90 subjects were administered TRESCELIUM™ as a preventive therapy. Of the 314 subjects that were infected with COVID-19 before receiving TRESCELIUM™, 309 subjects (98.40%) recovered after one dose of TRESCELIUM™ and did not require additional dosing. Five subjects (1.59%) required additional doses of TRESCELIUM™, and of those five subjects, two made a full recovery; three did not survive. Of the 90 subjects that were dosed with TRESCELIUM™ on a preventive basis, 70 subjects (77.77%) did not develop any symptoms of COVID-19. Twenty subjects developed symptoms and required at least one additional dose of TRESCELIUM™.

Figure 2A:
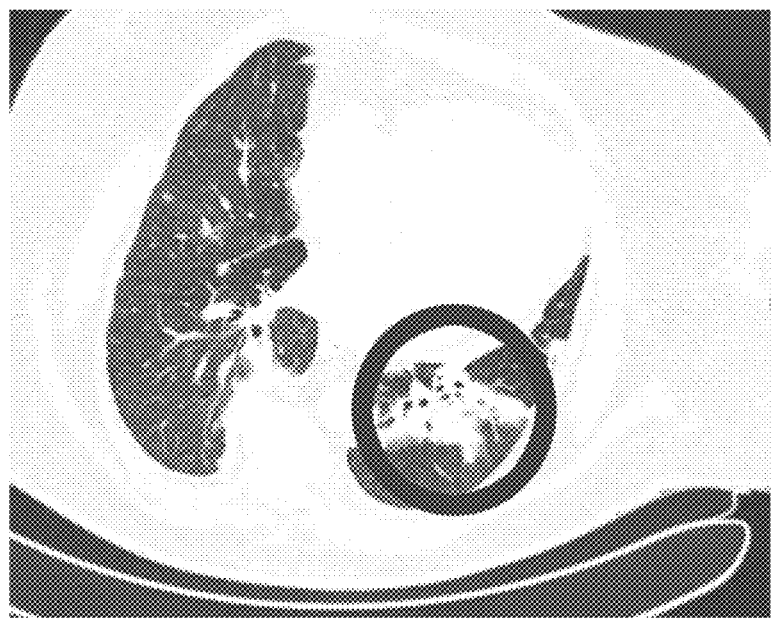
FIG. 2A-B show the effect of TRESCELIUM™ treatment on COVID-19 related lung damage in an 80-year-old female subject using MRI.
Figure 2B:
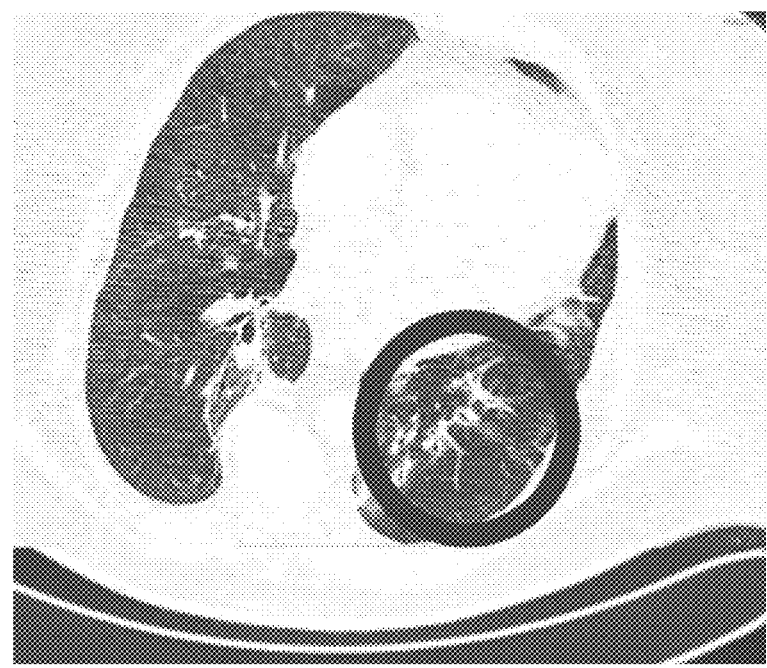
Figure 3A:
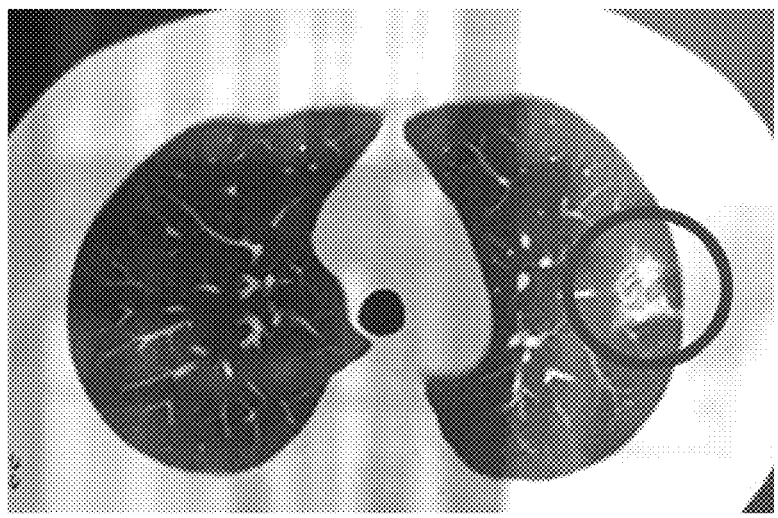
FIG. 3A-B show the effect of TRESCELIUM™ treatment on COVID-19 related lung damage in a 48-year-old male subject using MRI.
Figure 3B:
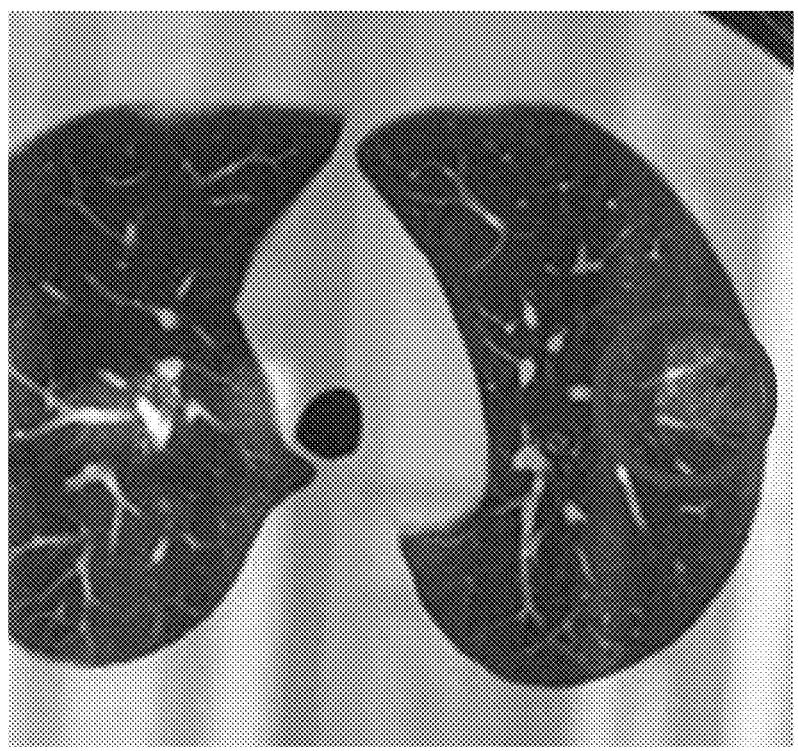

A total of 393 subjects (79 in Group One and 314 in Group Two) were deemed infected before treatment with TRESCELIUM™. Of all the subjects administered with TRESCELIUM™ as a treatment, 375 (95.42%) made a full recovery after a single dose of TRESCELIUM™, and another 15 (3.82%) required two or more doses of TRESCELIUM™ to return their $SpO_2$ levels back to normal. FIG. 2A-B and FIG. 3A-B show example MRI images of recovered lungs following a single dose of TRESCELIUM™ in subjects who had damaged lungs associated with COVID-19 pneumonia.

A total of 1,071 subjects (981 in Group One and 90 in Group Two) were given TRESCELIUM™ as a preventative therapy for COVID-19. Of the 1,071 subjects, 1,020 (95.24%) did not develop any symptoms of COVID-19. Fifty-one subjects (4.76%) ultimately developed symptoms and were given additional TRESCELIUM™ as a treatment therapy. The overall results for both treatment and preventive groups are presented in Table 9.

TABLE 9

TRESCELIUM™ Treatment and Preventive Results

Treatment Group (393 Subjects)

| Result | Recovered, 1 dose | Recovered, ≥2 doses | No recovery | Total |
|---|---|---|---|---|
| Total | 375 | 15 | 3 | 393 |

Preventive Group (1,071 Subjects)

| Result | No symptoms, 1 dose | Recovered, ≥2 doses | No recovery | Total |
|---|---|---|---|---|
| Total | 1020 | 48 | 3 | 1071 |

These results provide evidence for the preventive efficacy of TRESCELIUM™ with respect to COVID-19. Follow-up information was analyzed to know how many study participants became infected with COVID-19 in both groups. Treatment group participants also registered any side effects. No additional demographic studies were performed.

No specific studies on immunogenicity have been conducted. TRESCELIUM™ is not a vaccine, and its hypothesized mechanism of action is that it interferes with the binding of the ACE2/RBD Spike Protein. Therefore, immunogenic interactions are not the main therapeutic objective of TRESCELIUM™. On the other hand, it appears that TRESCELIUM™ inhibits viral replication and reduces viral load.

Safety Results

The safety of TRESCELIUM™ treatment was evaluated by side effects reported on the follow-ups of the treatment group. Subjects that received preventive treatment were exposed to one IV injection of 5.0 cc of TRESCELIUM™. Subjects that received treatment for COVID-19 were exposed to one or more IV injections of 10.0 cc of TRESCELIUM™.

Only 70 subjects from the 1,464-subject treatment group reported developing some type of adverse side effect in conjunction with administration of TRESCELIUM™. This represents a 4.78% rate of side effects that were mild and temporal. Not only was this an extremely low rate of adverse events, but the experienced adverse events were relatively minor in nature. No serious adverse events were reported, and no deaths directly attributed to TRESCELIUM™ were reported. A summary of the reported side effects is shown below in Table 10.

TABLE 10

Summary of Adverse Effects

| Reported Adverse Event | Subjects | Adverse Events (%) | Treatment Group (%) |
|---|---|---|---|
| Hypotension | 29 | 41% | 1.98% |
| Headache | 12 | 17% | 0.82% |
| Paresthesia | 11 | 16% | 0.75% |
| Diarrhea | 9 | 13% | 0.61% |
| Heat Sensation | 4 | 6% | 0.27% |
| Arterial Hypertension | 5 | 7% | 0.34% |

All the subjects reporting adverse events quickly recovered and returned to a blood oxygen level of 95% or greater. The overall low occurrence of adverse events supports a low risk profile of TRESCELIUM™ for use in the treatment of COVID-19. Therefore, the benefits of TRESCELIUM™ far exceed the potential safety risks of the drug from a safety perspective, and those benefits are greatly enhanced by the efficacy of the drug.

Based on the side effect results, TRESCELIUM™ is a safe preventive treatment against COVID-19 as no serious side effects nor deaths were registered after its application. The results of this study might be understood in context due to the lack of methodological controls (e.g., randomization and double blinded). Furthermore, the results cannot be generalizable to other populations, so more research is still needed.

Death and Comorbidities

During this study, the deaths of six participants due to COVID-19 were reported. All six subjects were part of a group of individuals deemed "compassionate treatments" meaning that they had $SpO_2$ levels below 85%, which is generally recognized as critical. The data for these six subjects are summarized below in Table 11.

TABLE 11

Subject Deaths from COVID-19 Related Factors

| Subject ID | Sex | Age (yrs) | Blood Type | $SpO_2$ at Treatment |
|---|---|---|---|---|
| P367 | Female | 67 | A+ | 56% |
| P331 | Male | 70-75 | Unknown | 82% |
| P65 | Female | 62-68 | Unknown | 75% |
| P64 | Female | 70 | Unknown | Unknown |
| C12 | Male | 65 | A+ | 83% |
| C159 | Male | 56 | A+ | 75% |

Subject "P367" presented with severely advanced COVID-19 infection. They received TRESCELIUM™ by IV injection at the same time having a 56% $SpO_2$ and heart rate of 107 beats per min. After receiving 10 mL of TRESCELIUM™, the $SpO_2$ increased to 67% and then to 71% $SpO_2$, with a heart rate of 94 beats per min. The next day, the $SpO_2$ dropped to 36% and heart rate to 116 beats per minute, and the died.

Subject "P331" had comorbidities including arterial hypertension and presented with severely advanced COVID-19 infection. His symptoms began with body pain, headache, and sore throat, and he had an $SpO_2$ of 82%. TRESCELIUM™ was administered and their $SpO_2$ level improved to 90%, but then dropped to 70%. The subject died three days later.

Subject "P65" had comorbidities including obesity and long-term diabetes. She presented with severely advanced COVID-19 infection and had symptoms including a headache and runny nose. An $SpO_2$ reading of 75% was measured at the time TRESCELIUM™ was injected. The died three days later with an $SpO_2$ reading of 35%.

Subject "P64" was in direct contact with people infected with COVID-19. She took TRESCELIUM™ as a preventive treatment. One month after treatment, COVID-19 symptoms developed, and the subject was treated by a pulmonologist who administered oxygen. No additional TRESCELIUM™ was administered. The subject continued to show low oxygen concentration readings for 20 days and died two weeks later.

Subject "C12" had comorbidities of arterial hypertension and diabetes. He received a preventive dose of TRESCELIUM™ and later became infected with COVID-19. Upon presentation, a low $SpO_2$ of 83% was detected with fever, nasal congestion, headache, anosmia, and ageusia. He continued to have $SpO_2$ readings of 83-85% with an oxygen concentrator. The subject was hospitalized with an $SpO_2$ reading of 80% and died 24 hours later.

Subject "C159" had comorbidities including morbid obesity, glucose intolerance, asthma, and multiple allergies. The subject received a first dose of TRESCELIUM™ with an SpO$_2$ of 75% and died two days later.

In each case, the attending physician concluded that the cause of death was not attributable to TRESCELIUM™, but instead was due to a combination of factors such as the existence of comorbidities, significantly advanced late-stage COVID-19 infections, high-risk categories including old age and weakened immune systems, and critically low SpO$_2$ levels. Traditionally, in individuals with SpO$_2$ levels below 85%, the rate of death is much higher than in subjects with higher SpO$_2$ levels. Subjects with oxygen levels of 85% and lower are traditionally intubated. Data show that as many as eight out of ten intubated subjects do not survive.

In addition, several subjects with non-COVID-19 related symptoms, but other comorbidities and diseases in advanced stages, were also given TRESCELIUM™ as a compassionate preventive treatment. These subjects had diseases that included renal disease, diabetes, hypertension, and cancer. Five of these subjects died as a result of their primary disease and not from causes related to COVID-19. Since this study included every individual that requested treatment, they were included in the study results. None of these five subjects developed COVID-19 symptoms. The data for these subjects are summarized below in Table 12.

TABLE 12

Comorbid Subject Deaths from COVID-19 Related Factors

| Subject ID | Sex | Age (yrs) | Blood Type | Comorbidities/Diseases |
|---|---|---|---|---|
| C962 | Male | 47 | A+ | Chronic renal disease |
| C420 | Female | 75 | Unknown | Diabetes |
| C307 | Female | 50 | Unknown | Acute renal failure |
| C679 | Female | 85 | A+ | Hypertension; gastric cancer; lithiasis; ascites |
| C906 | Female | 58 | Unknown | Hypertension |

Subject "C962" received treatment with TRESCELIUM™ on Aug. 20, 2020, as preventive care. The subject suffered from chronic renal disease and had been in treatment with dialysis for 10 years. He died three months later due to complications from chronic renal disease.

Subject "C420" was a longtime diabetes subject. She received TRESCELIUM™ as preventive care in December 2020. The subject died five months later due to complications from long-term diabetes.

Subject "C307" suffered from acute renal failure. The subject was assigned to receive TRESCELIUM™ while she was at the hospital, although the hospital staff did not confirm whether the subject received TRESCELIUM™. She died one month later due to renal failure.

Subject "C679" suffered from hypertension and was diagnosed with gastric cancer. She went to the emergency room due to complications from a varicose ulcer in the subject's leg in December 2020 and had received TRESCELIUM™ in June 2020 for preventive care. Following an ultrasound of the abdomen, the subject was diagnosed with lithiasis of the gallbladder and ascites. She died in January 2021 due to a heart attack.

Subject "C906" suffered from hypertension. She was were hospitalized after suffering heart failure and received TRESCELIUM™ in July 2020 as preventive care. The subject died six months later after being discharged from the hospital due to heart failure.

Furthermore, five separate subjects that had severe comorbidities or a very advanced infection of COVID-19 recovered successfully after taking TRESCELIUM™. The data for these five subjects are summarized below in Table 13.

TABLE 13

Recovered Subjects with Severe Comorbidities or Advanced infection

| Subject ID | Sex | Age (yrs) | Comorbidities/Diseases |
|---|---|---|---|
| C795 | Female | 27 | Arrhythmia; renal insufficiency |
| C65 | Female | 55 | Obesity; arterial hypertension; Type 2 diabetes; high cholesterol |
| C333 | Male | 56 | Hypertension; cardiac arrests |
| C914 | Female | 94 | Hypertension; obesity; ascites |
| C401 | Female | 75 | Hypertension; diabetes; osteoporosis |

Subject "C795" suffered from arrhythmia and renal insufficiency. She received TRESCELIUM™ for preventive treatment and did not show any SARS-COV-2 symptoms.

Subject "C65" suffered from obesity, arterial hypertension, Type 2 diabetes, and high cholesterol. She began with symptoms including headaches, dry cough, diarrhea, nausea, hyperemia, fever, and SpO$_2$ levels at 92%. Five days later, she received her first dose of TRESCELIUM™ intravenously. Within two days, her symptoms improved, and SpO$_2$ levels reached 98% on the eighth day of treatment.

Subject "C333" suffered from hypertension and had two cardiac arrests in previous surgeries. A month before his SARS-COV-2 symptoms started, he received preventive doses of TRESCELIUM™. When the symptoms began, he had headaches, fatigue, and SpO$_2$ levels were at 92%. When he received his second dose of TRESCELIUM™, his SpO$_2$ range was between 92-95%. The subject received multiple doses of TRESCELIUM™ intravenously for two consecutive months. One day, he experienced chest pain and had difficulty breathing. A CT scan revealed they had emphysematous bulla. He was discharged from the hospital.

Subject "C914" suffered from hypertension, obesity, and ascites. She received her first dose of TRESCELIUM™ after testing positive for SARS-COV-2. Her symptoms included difficulty breathing, hyporexia, articular pain, and fatigue. Her SpO$_2$ levels were at 88%, but SpO$_2$ levels reached 94% after receiving two more doses of TRESCELIUM™. She was discharged from the hospital.

Subject "C401" suffered from hypertension, diabetes, and osteoporosis. She presented no symptoms of SARS-COV-2, received her doses of TRESCELIUM™, and was discharged 21 days later without complications.

Example 6

Clinical Study: Comparative Study of TRESCELIUM™ and Control Treatments

This was a comparative study with two groups (treatment and control) with one TRESCELIUM™ treatment application, and follow-up at two and six months after application. The control group consisted of individuals who did not receive any type of treatment. The study lasted six months from July 2020 to January 2021. The study population consisted of mainly essential workers. Treatment was assigned given the likelihood to develop COVID-19 due, for example, to age and comorbidities. Non-treated workers were the control group. There was no randomization in this study. Individuals with existing diagnosis or symptoms of COVID-19 were not included in this study.

Treatment consisted of one unique IV dose of 5 cc (mL) TRESCELIUM™ for the treatment group. Groups were monitored constantly after treatment application. After two months, a survey was done to follow-up on the general condition of the subjects and to report any side effects. Subjects were assembled into groups for treatment. The time of application varied. All subjects in the treatment group received the same treatment of 5 cc (mL) of TRESCELIUM™. Subjects were free to withdraw from the study at any time without giving a reason. Subjects were advised that if they requested to withdraw from the study at any time, there would be no negative consequences. Data of pre-existing conditions were collected from the subjects in the TRESCELIUM™ test group and some subjects were also receiving treatment for diabetes, heart disease, asthma, etc.

The comparative study consisted of the following steps: group assignment; identification and personal information collected of subjects; treatment administration; two-month follow-up; six-month follow-up; data preparation; data analysis; and report writing (Table 14). This study was conducted at the following locations in Mexico: Culiacán, Sinaloa; Los Mochis, Sinaloa; Mazatlán, Sinaloa; Navojoa, Sonora; and Tijuana, Baja California Norte.

TABLE 14

Schedule of Examinations and Procedures in the Comparative Study

| Step | Study Day |
|---|---|
| Group assignment | 1 |
| Identification and personal information | 1 |
| Treatment administration | 14 |
| Two-month follow-up | 60 |
| Six-month follow-up | 180 |
| Data preparation | 190 |
| Data analysis | 270 |
| Report writing | 320 |

TRESCELIUM™ efficacy is understood as a reduction of positive symptoms of COVID-19 compared with no medication. TRESCELIUM™ safety is understood as minimum serious side effects when administered as a preventive treatment for COVID-19. The efficacy and safety measurements assessed included two parameters: subjects that developed COVID-19 and subjects that developed adverse reactions after receiving IV injections of TRESCELIUM™

Subjects were divided into treatment and control groups depending on their predisposition to develop COVID-19. These two groups had an equal number of participants at the start of the study (N=750 subjects per group). Data analyses consisted of descriptive statistics of subjects infected with COVID-19. To determine the efficacy of treatment, a chi-square was calculated as an independent test. The details of distribution, treatment, and withdrawal are presented below in Table 15. Regarding any study protocol deviations, only one participant in the treatment group did not meet entry criteria.

TABLE 15

Disposition of Subjects in the Comparative Study

| | Treatment Group (N = 750) | Control Group (N = 750) | Total (N = 1500) |
|---|---|---|---|
| Enrolled | 750 | 750 | 1500 |
| Received at least one injection | 749 | 0 | 749 |
| Received all injections and attended visit | 749 | 0 | 749 |

TABLE 15-continued

Disposition of Subjects in the Comparative Study

| | Treatment Group (N = 750) | Control Group (N = 750) | Total (N = 1500) |
|---|---|---|---|
| Completed visit | 749 | 750 | 1499 |
| Withdrawn | 1 | 0 | 1 |
| Lost to follow-up | 23 | 0 | 23 |
| Adverse event | 0 | 0 | 0 |
| Death | 0 | 0 | 0 |
| Other | 0 | 0 | 0 |

Efficacy Results

A total of 1,500 individuals were enrolled in the comparative study (61.6% were male and 38.4% were female). Only one subject withdrew before treatment, making the participant size of the treatment group 749 total individuals. In the treatment group, 376 subjects of the 749 were male and 373 were female. In the control group, 547 subjects of the 750 were male and 203 were female. All of the 1,499 participants completed the study. From the 749 participants of the treatment group, only 4.0% (30 participants) developed COVID-19 over the next six months and all participants survived. In the control group, 28.8% (216 participants) of the 750 developed COVID-19 over the next six months. The chi square analysis was computed to determine the independence between the results of treatment and control groups. According to this analysis, there were statistically significant differences for the rate of contagion between treatment and control groups ($X^2_{(1)}=120.47$, $p<0.001$). These results provide evidence for the preventive efficacy of TRESCELIUM™ with respect to COVID-19. Follow-up information was analyzed to know how many participants developed COVID-19 in both groups.

Safety Results

The safety of TRESCELIUM™ in the comparative study was evaluated by side effects reported on the follow-ups of the treatment group administered 5 cc of TRESCELIUM™. Only 25 subjects out of the entire 749-member treatment group reported developing some type of side effect after administration with TRESCELIUM™. This represents a 3.3% rate of reported side effects that included only mild and temporal symptoms. Not only was this an extremely low rate of adverse events, but the experienced adverse events were relatively minor in nature. No serious adverse events were reported. Additionally, no deaths attributed to TRESCELIUM™ treatment were reported. A summary of the reported side effects is included below in Table 16.

TABLE 16

Side Effects Observed in the Treatment Group

| Reported Adverse Event | No. of Subjects | Reported Adverse Events (%) | % Treatment Group |
|---|---|---|---|
| Hypotension | 4 | 16% | 0.50% |
| Headache | 8 | 32% | 1.06% |
| Paresthesia | 7 | 28% | 0.93% |
| Diarrhea | 4 | 16% | 0.50% |
| Heat Sensation | 2 | 8% | 0.27% |
| Arterial Hypertension | 0 | 0% | 0.00% |

All the subjects that reported adverse side effects quickly recovered and returned to a blood oxygen level of 95% or greater. The overall low occurrence of adverse events supports a low risk profile of TRESCELIUM™ for use in the prevention of COVID-19. The benefits of TRESCELIUM™ far exceed the potential safety risks of the drug from a safety perspective, and those benefits are greatly enhanced by the effectiveness of the drug.

The results of this comparative study demonstrate that TRESCELIUM™ is an effective and safe option for COVID-19 prevention. The results of the study might be taken with reservation due to the lack of methodological control (randomization, double blinded, etc.). Furthermore, the results cannot be generalizable to other populations, so more research is still needed.

Example 7

TRESCELIUM™ Improves Respiratory Function in Subjects with Respiratory Comorbidities Of the 2214 subjects treated with TRESCELIUM™, 46 reported having respiratory comorbidities. Subjects (46) were surveyed to investigate whether they had general improvement of their respiratory ailments following treatment with TRESCELIUM™. Thirty subjects (65%) responded. Of the responding subjects, 22 (73%) reported an overall improvement to their respiratory issues, 8 (27%) reported no changes; and no subject reported further deterioration of their respiratory ailments.

Subjects Responding 30 (65%)
Subjects No Responding 16 (35%)
Total Subjects Surveyed 46 (100%)
Of the 30 subjects responding to the Survey:
Subjects showing improvements 22 (73%)
Subjects that had no change 8 (27%)
Subjects feeling worse 0 (0%)
Total Subjects 30 (100%)

What is claimed:

1. A pharmaceutical composition comprising:
about 5-15% by mass procaine or a pharmaceutically acceptable salt thereof;
about 85-95% by mass of a tri- or tetra-peptide comprising one or more glutamate residues or a pharmaceutically acceptable salt thereof;
about 0.01-0.1% by mass DNase 1.

2. The composition of claim 1, wherein the composition further comprises RNase A.

3. The composition of claim 1, wherein the composition further comprises one or more pharmaceutically acceptable excipients.

4. The composition of claim 1, wherein the composition comprises:
0.71 mM procaine; 5.4 mM glutathione; and 0.3 μM DNase 1.

5. The composition of claim 1, wherein the composition comprises:
   about 8-10% by mass procaine or a pharmaceutically acceptable salt thereof;
   about 88-92% by mass of a tri- or tetra-peptide comprising one or more glutamate residues or a pharmaceutically acceptable salt thereof; and
   about 0.02-0.08% by mass DNase 1.

6. The composition of claim 1, wherein the composition comprises:
   about 9% by mass procaine or a pharmaceutically acceptable salt thereof;
   about 90% by mass of a tri- or tetra-peptide comprising one or more glutamate residues or a pharmaceutically acceptable salt thereof; and
   about 0.05% by mass DNase 1.

7. The composition of claim 6, wherein the composition further comprises about 0.5% by mass RNase A.

8. The composition of claim 1, wherein the composition comprises about 0.1-0.3 mg/ml procaine; about 1-3 mg/mL of a tri- or tetra-peptide comprising one or more glutamate residues; and about 0.0008-0.0012 mg/mL DNase 1.

9. The composition of claim 8, wherein the composition comprises about 0.2 mg/ml procaine; about 2 mg/ml of a tri- or tetra-peptide comprising one or more glutamate residues; and about 0.001 mg/mL DNase 1.

10. The composition of claim 9, wherein the composition further comprises about 0.01 mg/mL RNase A.

11. The composition of claim 1, wherein the tri- or tetra-peptide comprising one or more glutamate residues comprises glutathione, E-E-X, X-E-E, E-X-E, E-E-X-X, E-E-X-E, E-X-E-E, E-X-X-E, X-E-E-E, or X-X-E-E, wherein E is a glutamate residue and X is an aliphatic amino acid.

12. The composition of claim 11, wherein the tri- or tetra-peptide comprising one or more glutamate residues comprises glutathione ($\gamma$E-C-G).

13. The composition of claim 1, wherein the composition comprises: 9.0% by mass procaine; 90.4% by mass glutathione; and 0.05% by mass DNase 1.

14. The composition of claim 1, wherein the composition comprises: 0.17 mg/mL procaine; 1.7 mg/mL glutathione; and 0.001 mg/mL DNase 1.

15. The composition of claim 1, wherein the composition is a liquid suitable for injection or inhalation.

16. The composition of claim 1, wherein the composition further comprises one or more stem cells.

17. The composition of claim 16, wherein the stem cell is an embryonic stem cell, perinatal stem cell, adult stem cell, induced pluripotent stem cell, tissue-specific stem cell, mesenchymal stem cell, hematopoietic stem cell, neural stem cell, or epithelial stem cell.

18. The composition of claim 16, wherein the stem cell is a subject-derived stem cell.

* * * * *